United States Patent
Sra et al.

(10) Patent No.: US 10,258,302 B2
(45) Date of Patent: Apr. 16, 2019

(54) RAPID 3D CARDIAC PARAMETER MAPPING

(71) Applicant: APN Health, LLC, Pewaukee, WI (US)

(72) Inventors: Jasbir Sra, Pewaukee, WI (US);
Shivani Kohut, Fayetteville, NC (US);
Donald Brodnick, Cedarburg, WI (US)

(73) Assignee: APN Health, LLC, Pewaukee, WI (US)

( * ) Notice: Subject to any disclaimer, the term of this patent is extended or adjusted under 35 U.S.C. 154(b) by 153 days.

(21) Appl. No.: 15/487,245

(22) Filed: Apr. 13, 2017

(65) Prior Publication Data

US 2018/0296176 A1    Oct. 18, 2018

(51) Int. Cl.
*A61B 6/00*     (2006.01)
*A61B 5/0408*   (2006.01)
(Continued)

(52) U.S. Cl.
CPC .............. *A61B 6/503* (2013.01); *A61B 5/044* (2013.01); *A61B 5/0432* (2013.01);
(Continued)

(58) Field of Classification Search
None
See application file for complete search history.

(56) References Cited

U.S. PATENT DOCUMENTS 7,995,819 B2    8/2011 Vaillant et al.
8,224,432 B2    7/2012 MacAdam et al.
(Continued)

FOREIGN PATENT DOCUMENTS

EP    2689722    1/2014
EP    2848191    3/2015
(Continued)

*Primary Examiner* — Brian T Gedeon
(74) *Attorney, Agent, or Firm* — Jansson Munger McKinley & Kirby Ltd.

(57) ABSTRACT

A method for generating a 3D map of a cardiac parameter in a region of a living heart, the method using single-plane fluoroscopic images and comprising: (a) placing a plurality of catheters each having one or more radio-opaque sensors into the region such that the locations of the sensors geometrically span the region; (b) capturing a first-view digitized 2D image of the region from a first fluoroscope positioned at a first angle; (c) identifying each of the plurality of sensors in the first-view image; (d) capturing a second-view digitized 2D image of the region from a second fluoroscope positioned at a second angle which is different from the first angle; (e) identifying each of the plurality of sensors in the second-view image; (f) associating each of the plurality of identified sensors in the second-view image with its corresponding identified sensor in the first-view image; (g) sensing and storing values of the cardiac parameter with each of the plurality of sensors; (h) determining the 3D location of each of the plurality of sensors from the first-view and second-view images using back-projection calculations; (i) associating each of the parameter values with its corresponding sensor location; (j) generating the parameter map from the first-view and second-view images; and (k) displaying the parameter map on a display device.

35 Claims, 16 Drawing Sheets
(2 of 16 Drawing Sheet(s) Filed in Color)

(51) Int. Cl.
    *A61B 5/044*    (2006.01)
    *A61B 5/0432*    (2006.01)
    *A61M 25/01*    (2006.01)
    *A61B 90/00*    (2016.01)

(52) U.S. Cl.
    CPC ........ *A61B 5/04085* (2013.01); *A61B 6/4266* (2013.01); *A61B 6/463* (2013.01); *A61B 6/466* (2013.01); *A61B 6/481* (2013.01); *A61B 6/487* (2013.01); *A61B 6/5205* (2013.01); *A61B 6/5217* (2013.01); *A61M 25/0108* (2013.01); *A61B 2090/3966* (2016.02)

(56) References Cited

U.S. PATENT DOCUMENTS

| | | | |
|---|---|---|---|
| 8,275,452 B2 | 9/2012 | MacAdam et al. | |
| 8,306,612 B2 | 11/2012 | MacAdam | |
| 8,768,440 B1 | 7/2014 | Brodnick et al. | |
| 8,788,024 B1 | 7/2014 | Brodnick et al. | |
| 8,812,091 B1 | 8/2014 | Brodnick | |
| 8,948,856 B2 | 2/2015 | Brodnick et al. | |
| 8,948,857 B2 | 2/2015 | Brodnick | |
| 9,186,081 B2 | 11/2015 | Alfonso et al. | |
| 9,314,179 B1 | 4/2016 | Brodnick et al. | |
| 9,392,951 B2 | 7/2016 | Greenspan et al. | |
| 9,986,931 B2 * | 6/2018 | Sra | A61B 6/022 |
| 2003/0220555 A1 | 11/2003 | Heigl et al. | |
| 2013/0243153 A1 | 9/2013 | Sra et al. | |
| 2016/0106336 A1 | 4/2016 | Li et al. | |
| 2016/0235383 A1 | 8/2016 | Bar-Tal et al. | |
| 2017/0251942 A1 | 9/2017 | Brodnick et al. | |

FOREIGN PATENT DOCUMENTS

| | | |
|---|---|---|
| WO | 2015130824 | 9/2015 |
| WO | 2015148470 | 10/2015 |

\* cited by examiner

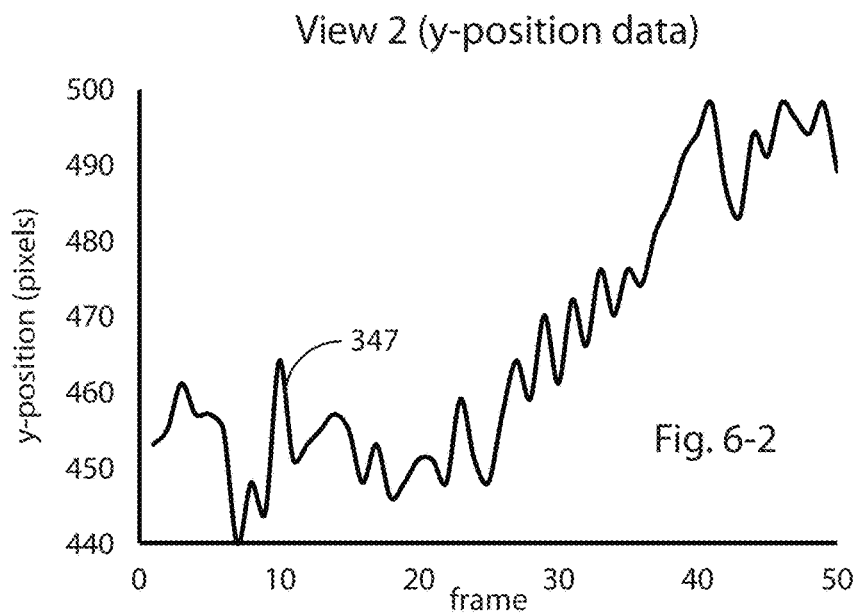
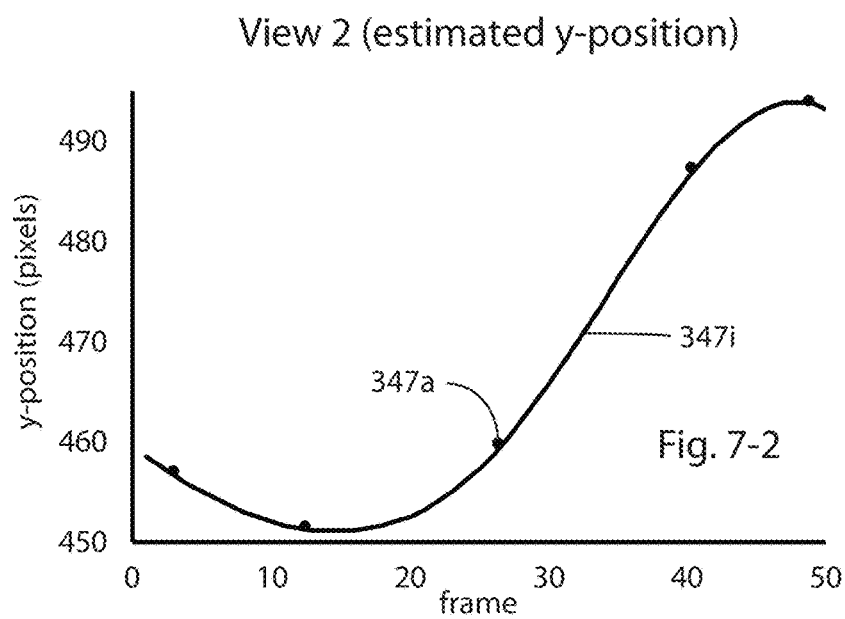

RAPID 3D CARDIAC PARAMETER MAPPING

FIELD OF THE INVENTION

This invention is related generally to the field of medical fluoroscopy, and more particularly to technology for rapid measurement and display of cardiac parameter values within a living heart.

BACKGROUND OF THE INVENTION

Mapping of physiological structures and various physiological parameters sensed within the body is an important technological component of the practice of medicine. Such mapping procedures can be time-consuming, and often the imaging modality utilized to capture geometric data for the mapping process requires patient exposure to X-rays. The time during which a patient undergoes a mapping procedure and the accompanying interventional treatment and the patient's total exposure to X-ray radiation are both important risk factors for medical mapping procedures; both time and X-ray exposure are desirably minimized.

The inventive method disclosed herein is directed toward generating such maps much more rapidly, and although the inventive method may be applicable to the mapping of physiological parameters other than parameters associated with the heart, much of the disclosure herein is made within the area of cardiology. Electrocardiology is an area of cardiology in which this invention is particularly and advantageously applicable.

U.S. patent application Ser. No. 13/607,163 (Sra et al.), titled "Automatically Determining 3D Catheter Location and Orientation Using 2D Fluoroscopy Only" and published as Published Application No. 2013/0243153, discloses a novel system for extracting the third dimension from a stream of single-plane fluoroscopic images. The system uses only 2D image information to determine the 3D location and orientation of a catheter during medical procedures. For convenience, such system may be called the Catheter Tip 3D Location System and may be referred to herein as C3DLS to shorten the terminology. The Sra et al. application is hereby incorporated herein for reference in its entirety. The initialization and calibration process within C3DLS incorporates the use of two single-plane fluoroscopic images of objects such as catheters outside the living body taken from different angles. Thereafter, the method disclosed in Sra et al. uses single-plane fluoroscopic images taken only from one angle to determine the 3D location and orientation of objects within a living body.

The novel method disclosed in the Sra et al. document involves building a map point-by-point as do many other methods directed at map generation. There is therefore an important need to reduce the time and radiation exposure involved in map generation. It is also quite common for cardiac rhythms to change during a medical procedure, and such an occurrence creates the need for the physician to be able to respond in order to learn more about the patient's condition. Maps generated on a point-by-point basis cannot be generated fast enough to be useful in such circumstances.

United States Published Application No. 2016/0235383 discloses a system for compensating for heart movement using coronary sinus catheter images. Focusing on compensating for the motion of an individual catheter, no cardiac parameter maps are generated which are derived from single-plane fluoroscopic images.

With the present invention, in addition to the dramatic decrease in the time required to generate an initial 3D parameter map, it has been found that in some cases, the cardiologist is able to determine all or nearly all of the scope of the medical situation at hand with the initial rapidly-constructed map generated and displayed by the inventive method disclosed herein. If this is not the case, at least such a map may still be highly beneficial by pointing to an important area of concern, indicating to the cardiologist the direction of the next steps to be taken for the patient. In every case, procedure time and total X-ray exposure have been dramatically reduced, both such reductions being highly advantageous to the patient.

OBJECTS OF THE INVENTION

It is an object of this invention to provide a method for rapidly determining the 3D locations of a plurality of radio-opaque sensors placed in a living heart by using single-plane fluoroscopic images from two different angles.

Another object of this invention is to provide a method which associates a sensed cardiac parameter with the determined 3D locations and generates and displays the parameter data as 3D maps. A further related object is to provide such a method in which the rapid determination of locations provides simultaneous determination of location and capture of sensor data such that cardiac parameter mapping is essentially a parallel process for the plurality of map points.

Another object of this invention is to provide a method which accurately generates and displays such 3D maps when the two angular fluoroscopic views are captured sequentially.

Yet another object of this invention is to provide a method which optimizes the determination of 3D locations of the sensors in the presence of cardiac and respiratory motion.

A further object of this invention is to provide a method for rapid 3D mapping which operates in conjunction with a fluoroscopic system configured to automatically determine the 3D location and orientation of a radio-opaque medical object in a living system using only single-plane fluoroscopy.

Another object of this invention is to provide a method which, when the cardiac parameter values change, generates a new parameter map using the sensor location previously determined and updated cardiac parameter values.

Another object of this invention is to provide a method for rapid generation and display of local activation time (LAT) maps Yet another object of this invention is to provide a method for rapid generation and display of cardiac parameter maps with more than one such map displayed at the same time.

Another object of this invention is to provide a method which permits generation and display of LAT maps using electrical signals during one cardiac cycle.

These and other objects of the invention will be apparent from the following descriptions and from the drawings.

SUMMARY OF THE INVENTION

The present invention is a method for generating a 3D map of a cardiac parameter in a region of a living heart using single-plane fluoroscopic images. The method comprises: (a) placing a plurality of catheters each having one or more radio-opaque sensors into the region such that the locations of the sensors geometrically span the region; (b) capturing a first-view digitized 2D image of the region from a first fluoroscope positioned at a first angle; (c) identifying each of the plurality of sensors in the first-view image; (d) capturing a second-view digitized 2D image of the region from a second fluoroscope positioned at a second angle which is different from the first angle; (e) identifying each of the plurality of sensors in the second-view image; (f) associating each of the plurality of identified sensors in the second-view image with its corresponding identified sensor in the first-view image; (g) sensing and storing values of the cardiac parameter with each of the plurality of sensors; (h) determining the 3D location of each of the plurality of sensors from the first-view and second-view images using back-projection calculations; (i) associating each of the parameter values with its corresponding sensor location; (j) generating the parameter map from the first-view and second-view images; and (k) displaying the parameter map on a display device.

In highly-preferred embodiments, the first and second fluoroscopes are the same fluoroscope, and the second-view image is captured subsequent to the capture of the first-view image. In some such highly-preferred embodiments, capturing the first-view image includes capturing a first burst of images and selecting the first-view image from among the first burst of images, and capturing the second-view image includes capturing a second burst of images and selecting the second-view image from among the second burst of images.

Some preferred embodiments of the inventive method include determining a cardiac phase and a respiratory phase for each captured first-view and second-view image. In some embodiments, selecting the first-view and second-view images includes the steps of (a) identifying candidate images in the first and second bursts of images for which a cardiac-phase criterion and a respiratory-phase criterion are satisfied and (b) selecting a first-view image and a second-view image from the candidate images using a similarity criterion based on the cardiac phase and respiratory phase of the candidate images.

In some preferred embodiments, the cardiac phase of each image is estimated using an R-wave detector to identify R-waves and measure R-wave intervals, and in some of these embodiments, the cardiac phase of an image is the percentage of time, along the R-wave interval, at which an image was captured. Further, in some such embodiments, the cardiac-phase criterion is satisfied if the cardiac phase of an image is between 30% and 80%.

In some preferred embodiments of the inventive method, the respiratory phase of an image is estimated from the locations acquired from a burst of images of one of the plurality of sensors to determine maximum exhalation and maximum inhalation displacement and determine a percentage of exhalation/inhalation range for the image. In some of these embodiments, the respiratory-phase criterion is satisfied when the respiratory phase of an image is between 0% and 20% of maximum exhalation.

In some highly-preferred embodiments, the selecting step further includes (1) for each pair of a candidate first-view image $I_i$ and a candidate second-view image $I_j$, computing the sum of the absolute value of the difference between the cardiac phases of images $I_i$ and $I_j$ and the absolute value of the difference between the respiratory phases of images $I_i$ and $I_j$, and (2) selecting the pair of first-view and second-view images for which the sum is the minimum. In some of these embodiments, the cardiac-phase difference and respiratory-phase difference are given relative weights prior to summing.

In preferred embodiments of the invention, the sensors are cardiac electrodes which capture electrical signals from the living heart. In some highly-preferred embodiments, one of the plurality of electrodes is a reference electrode and the cardiac parameter mapped is local activation time (LAT). In some of these embodiments, one or more additional LAT maps are generated using the electrode locations previously determined, the reference electrode for each such additional LAT map being selected from all electrodes in the plurality of electrodes not currently being used as a reference electrode. Also, in some such embodiments, displaying the parameter map includes displaying one or more LAT maps at the same time.

In some embodiments of the inventive method, the LAT map is generated using the electrode locations previously determined and the electrical signals from the plurality of electrodes during one cardiac cycle. In some of these embodiments, the one cardiac cycle is selected from the stored LAT values.

Some preferred embodiments of the inventive method include determining changes in the cardiac parameter values based on update criteria and, when a change occurs, generating a new parameter map using the sensor locations previously determined and updated cardiac parameter values. In some of these embodiments, the update criteria are update thresholds and determining changes in the cardiac parameter includes computing for each sensor the difference between the updated parameter value and a previous parameter value and when at least one such difference is greater than an update threshold, generating the new parameter map. In some such embodiments, the update threshold is the same value for each sensor, and in such embodiments, the update threshold for each sensor is dependent on the parameter values associated with the corresponding sensor. In such parameter-value update thresholds, the update threshold for each sensor may be twice the standard deviation of the parameter values associated with the corresponding sensor.

In some highly-preferred embodiments, the single-plane fluoroscopic images are captured by a fluoroscopic system configured to automatically determine the 3D location and orientation of a radio-opaque medical object in a living system using only single-plane fluoroscopy, such system using the determination of the 3D locations of the sensors as a portion of its initialization step. In some of these embodiments, the radio-opaque medical object is a mapping sensor, and the method includes adding one or more supplemental 3D locations of the mapping sensor and the corresponding parameter values associated with the supplemental 3D locations to the parameter map and storing the supplemental 3D locations and corresponding parameter values.

In another aspect of the invention, the method for generating a 3D parameter map of a cardiac parameter in a region of a living heart using single-plane fluoroscopic images comprises: (a) placing a plurality of catheters each having one or more radio-opaque sensors into the region such that the locations of the sensors geometrically span the region; (b) capturing a burst of first-view digitized 2D images of the region from a fluoroscope positioned at a first angle; (c) capturing a burst of second-view digitized 2D images of the region from a fluoroscope positioned at a second angle different from the first angle; (d) selecting a first-view image and a second-view image from the bursts such that the difference between a measure of the cardio-respiratory phase of the selected first-view image and the cardio-respiratory phase of the second-view image is minimized; (e) identifying each of a subset of sensors in the selected first-view and second-view images and associating each of the identified sensors in the second-view image with its corresponding identified sensor in the first-view image; (f) determining the 3D location of each of the identified sensors from the selected first-view and second-view images using back-projection calculations; (g) sensing and storing values of the cardiac parameter with each of the identified sensors; (h) associating each of the parameter values with its corresponding sensor location; (i) generating the parameter map from the selected first-view and second-view images; and (j) displaying the parameter map on a display device.

In yet another aspect of the invention, the invention is a method for generating a 3D map of a cardiac parameter in a region of a living heart into which region a plurality of catheters, each having one or more radio-opaque sensors, has been placed such that the locations of the sensors geometrically span the region. The method uses single-plane fluoroscopic images and comprises the steps of: (a) capturing a first-view digitized 2D image of the region from a first fluoroscope positioned at a first angle; (b) identifying each of the plurality of sensors in the first-view image; (c) capturing a second-view digitized 2D image of the region from a second fluoroscope positioned at a second angle which is different from the first angle; (d) identifying each of the plurality of sensors in the second-view image; (e) associating each of the plurality of identified sensors in the second-view image with its corresponding identified sensor in the first-view image; (f) sensing and storing values of the cardiac parameter with each of the plurality of sensors; (g) determining the 3D location of each of the plurality of sensors from the first-view and second-view images using back-projection calculations; (h) associating each of the parameter values with its corresponding sensor location; (i) generating the parameter map using first-view and second-view images; and (j) displaying the parameter map on a display device.

The terms "image" and "frame" are used interchangeably herein and unless otherwise noted, refer to sets of digitized data captured from a conventional fluoroscope. The images or frames are two-dimensional arrays of pixels (picture elements), each pixel having an associated image-intensity value.

The terms "X-ray" and "fluoroscopic" are used interchangeably herein.

In referring to the locations of the sensors, the term "geometrically span the region" as used herein means, as hereafter explained, that the sensors are placed in the region of the living heart such that the sensors are in positions associated with known structure of the heart and that (1) when the region is planar, there are at least three sensors at three corresponding 3D-locatable points, and (2) when the region is a volume, there are at least four sensors which are 3D-locatable at four corresponding non-coplanar points. The region spanned by the sensors is typically not the entirety of a region associated with a physiological structure but is a region (or sub-region) which, when visualized, is of medical interest to the cardiologist, made such by virtue of the points being associated with known structure of the heart. Thus, the 3D parameter maps generated and displayed may be planar or volumetric. When the region geometrically spanned is planar, the map is nevertheless a 3D map in that 3D location/orientation of the planar region is of importance.

The term "burst of images" as used herein refers to a set of sequential fluoroscopic images captured over a period of time, the frequency of which is typically determined by the frame-rate setting of the fluoroscope.

The term "sensing" related to a cardiac parameter as used herein refers both to the physiological measurements and the processing of such measurements to produce the cardiac parameter.

The terms "location" and "position" may be used interchangeably herein to refer to the 3D coordinates of an object such as a radio-opaque sensor.

The term "exhalation/inhalation range" as used herein refers to the distance between the external 2D positions of a sensor as it moves from image-to-image within a sequence of images.

The term "cardio-respiratory phase" as used herein refers to the phase of combined cardiac and respiratory motions. Therefore, as used herein, minimizing the difference between the cardio-respiratory phases of two images may also include minimizing a combination of measures of both cardiac phase and respiratory phase.

The term "reference-signal fiducial" as used herein refers to any of several specific points in time within a cardiac electrical signal between which the cycle length of such a signal is measured. Among these specific points in time are (a) the point of maximum negative velocity, (b) the point of intrinsic deflection, and (c) the point of peak voltage.

The terms "method step," "method element," and "functional element" or other similar terms may be used interchangeably herein to refer to portions of the inventive method.

BRIEF DESCRIPTION OF THE DRAWINGS

The present invention uses two X-ray images from different angles, View 1 and View 2. In the drawings, when there are corresponding figures for the two views, the numbering convention used herein is that such two-view figures are numbered N-1 and N-2 to indicate that figures relate to View 1 and View 2, respectively.

FIGS. 4-1 and 4-2 are representative X-ray images of a patient's chest in AP (anterior-posterior) and LAO (left anterior oblique) positions, respectively, with a plurality of cardiac catheters in position in the patient. Each of the two images is one image from a burst of images from a first angle (View 1) and one image from a burst of images from a second angle (View 2), respectively.

FIGS. 6-1 and 6-2 are plots of exemplary y-position data for the mapping/ablation catheter (lower right sensor of sensors 337 in the images of FIGS. 4-1 and 4-2) for fifty (50) frames of a View 1 burst and fifty (50) frames of a View 2 burst, respectively. Note that FIGS. 6-1 and 6-2 are paired with FIGS. 7-1 and 7-2, respectively, and are therefore on different pages, as are FIGS. 7-1 and 7-2.

FIGS. 7-1 and 7-2 are plots of the y-position data of FIGS. 6-1 and 6-2, respectively, which has been smoothed and interpolated to generate an estimate of respiratory phase for each image.

FIGS. 8-1 and 9-1 are plots of the respiratory and cardiac phases for each of the fifty View 1 frames and fifty View 2 frames, respectively. The values of both the cardiac phase and respiratory phase have been normalized onto 0-1 scales. Note that FIGS. 8-1 and 8-2 are paired with FIGS. 9-1 and 9-2, respectively, and are therefore on different pages, as are FIGS. 9-1 and 9-2.

FIGS. 8-2 and 9-2 are plots of the respiratory and cardiac phases for View 1 and View 2 frames, respectively. In each such figure, frames which satisfy a cardiac-phase criterion are plotted, and frames which satisfy a respiratory-phase criterion are also plotted, FIG. 8-2 for View 1 images and FIG. 9-2 for View 2 images. Such frames illustrate the results of the determination of sets of candidate View 1 and View 2 frames for final selection as a pair of images from which to determine the 3D location of each of the plurality of sensors using back-projection calculations.

FIGS. 11-1 and 11-2 are portions of the same X-ray images as in FIGS. 4-1 and 4-2, respectively, each having a subset of the plurality of sensors identified in View 1 and View 2. Only the regions of such images which contain the cardiac catheter electrodes are shown.

FIG. 13A shows an anterior/posterior (AP) view of this map; FIG. 13B shows a right lateral (RL) view; and FIG. 13C shows a left lateral (LL) view.

DETAILED DESCRIPTION OF PREFERRED EMBODIMENTS

This invention is a method for rapidly generating a 3D map of a cardiac parameter in a region of a living heart into which region a plurality of radio-opaque sensors has been placed. The method uses single-plane fluoroscopic images to determine the 3D locations of each of the plurality of sensors from a pair of single-plane fluoroscopic images and then generates and displays the physiological-parameter map by associating the sensed values of the cardiac parameter with the 3D locations of the sensors.

One important aspect of this inventive method is its application within a system which processes X-ray image intensity data within a stream of fluoroscopic images captured only from a single-plane fluoroscope positioned at a fixed angle. Such a system, described in Sra et al., automatically determines the 3D location and orientation of a radio-opaque medical object in a living system by (a) using pixel-level geometric calculations by statistically combining a plurality of raw-data cross-sectional intensity profiles to estimate image dimensions and (b) applying conical projection and radial elongation corrections to these image measurements in order to extract 3D position information of an object such as a medical catheter from the stream of 2D images.

The present invention, although not limited to applications within a C3DLS system, may be used within the initialization steps of C3DLS and may also be used during C3DLS operation as will be described herein.

Figure 1:
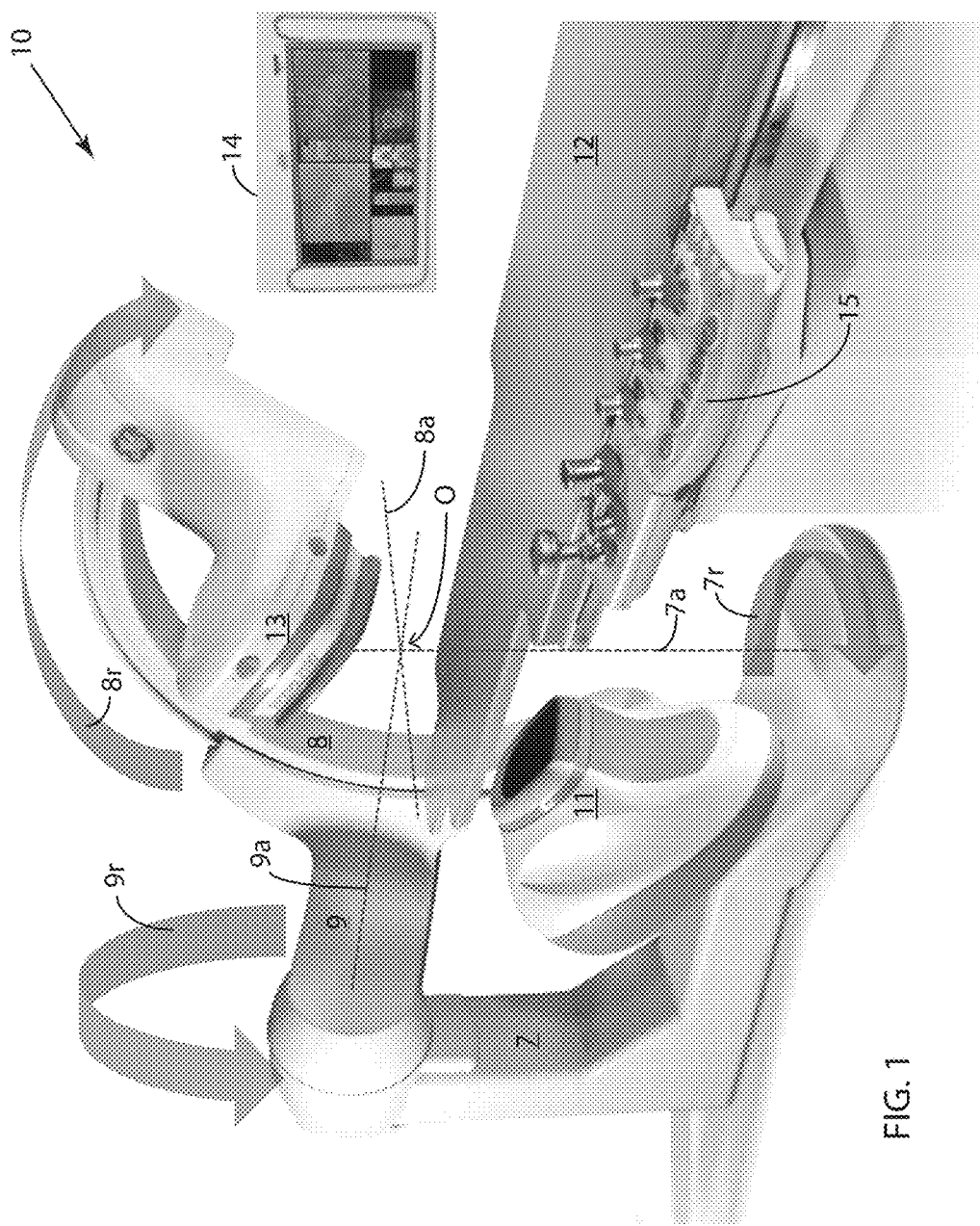
FIG. 1 is an illustration of an exemplary conventional X-ray machine (fluoroscope). The exemplary machine shown in FIG. 1 is a GE Innova 2100 system.

FIG. 1 illustrates an exemplary conventional fluoroscopic system 10 used to acquire 2D fluoroscopic image data. The imaging process for conventional fluoroscopy involves an X-ray source 11 which sends an X-ray beam through a patient (not shown) on a table 12. An X-ray detector 13, which may be a flat-panel detector or an image intensifier/video camera assembly, receives the X-rays transmitted through the patient and converts the X-ray energy into an image.

X-ray source 11 and X-ray detector 13 are mounted on opposite ends of a C-arm 8. Detector 13 may perform the conversion using an X-ray detection layer that either produces light or releases electrons when stimulated by X-rays, and a light-to-electron conversion layer, e.g., photodiodes or electron collection layer, as appropriate, in which an electrical charge signal proportional to X-ray signal intensity in each picture element (pixel) is collected. Analog-to-digital (A/D) conversion then produces a digital image. Whatever type of X-ray detector 13 is employed, the resulting digital image is then processed, possibly stored, and displayed on a screen 14. A control panel is shown at 15. Images may then be displayed on a computer display 14.

Figure 2:
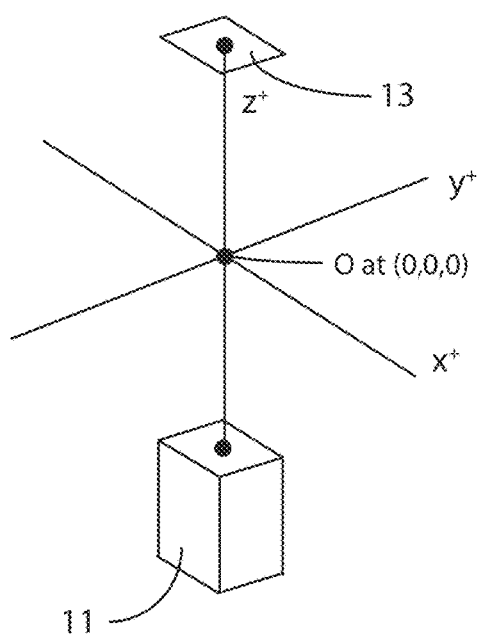
FIG. 2 illustrates an exemplary set of axes which define the 3D coordinates of a procedural fluoroscopic suite. Each element of the suite has a position which can be described by coordinates in this coordinate system. The positive direction of each axis is indicated.

FIG. 2 illustrates an exemplary coordinate system for fluoroscopic system 10. The three axes are shown by the solid lines in FIG. 2. The z-axis is defined from X-ray source 11 to the center of X-ray detector 13 with the X-ray beam vertical and perpendicular to table 12 (the AP position—anterior-posterior position). The positive ($z^+$) direction is defined by the patient's chest (anterior) with $z^-$ as the patient's back (posterior). X-ray table 12 defines an x-axis and a y-axis. The y-axis is parallel to the table with the positive direction ($y^+$) being toward the patient's head (superior). The x-axis is perpendicular to both the y-axis and the z-axis with the positive direction ($x^+$) being to the patient's left. The intersection of the axes is at an origin O, at (0,0,0) of the 3D space defined by axes x, y and z. Control panel 15 is configured to translate the patient along all three of the axes (three translational degrees-of-freedom) as defined above.

As shown in FIG. 1, fluoroscopic system 10 is also configured to rotate around three axes 7a, 8a, 9a (indicated by dotted lines) as a further means to permit the desired positioning of the patient in the field-of-view of the fluoroscopic system 10 and to provide adequate room for medical personnel to perform the desired procedure. In fluoroscopic system 10, origin O is also the center-of-rotation of these three rotational degrees-of-freedom, i.e., the isocenter (center-of-rotation of the X-ray beam central ray) of fluoroscopic system 10. Fluoroscopic system 10 includes a base 7 which is able to rotate on the floor around axis 7a, C-arm 8 which is able to rotate around axis 8a, and an L-arm 9 which is able to rotate around axis 9a. Arrows 7r, 8r and 9r indicate the motion possible with these three rotational degrees-of-freedom.

Note that the three axes x,y,z which define the coordinate system within fluoroscopic system 10 are not necessarily the same as axes 7a,8a,9a since rotations around such axes change the relative positions of theses axes with respect to axes x,y,z. Of course, coordinate systems are relative, and other coordinate systems may be used; the exemplary set of axes described above is not intended to be limiting. Also, not all fluoroscopic systems are configured with all of the translational and rotational degrees-of freedom which are described in exemplary fluoroscopic system 10, and such set of degrees-of-freedom is not intended to be limiting.

Initialization and calibration within C3DLS 20 (see FIG. 15 for reference number 20 referring to C3DLS) employs in just this one instance a second single-plane image taken from a different angle of C-arm 8. Known mathematical techniques are used to measure effective X-ray dimensions using two-view projection calculations in element 39. In elements 41A and 41B, maximum and minimum catheter-tip image area criteria are set (element 41A), and a maximum catheter-tip image length criterion is set (element 41B). The measurements of functional element 39 are performed by placing a catheter on table 12 (e.g., on top of the patient or directly on table 12 in its sterile package) between X-ray source 11 and X-ray detector 13, and two images from different known C-arm 8 angular positions and geometry are acquired by video acquisition in functional block 37. The analytic methods to determine the 3D coordinates and the effective dimensions of catheter tip 18 using data from two 2D images of the same object taken from two different angles are well-known to those skilled in the art of mathematics.

Figure 3:
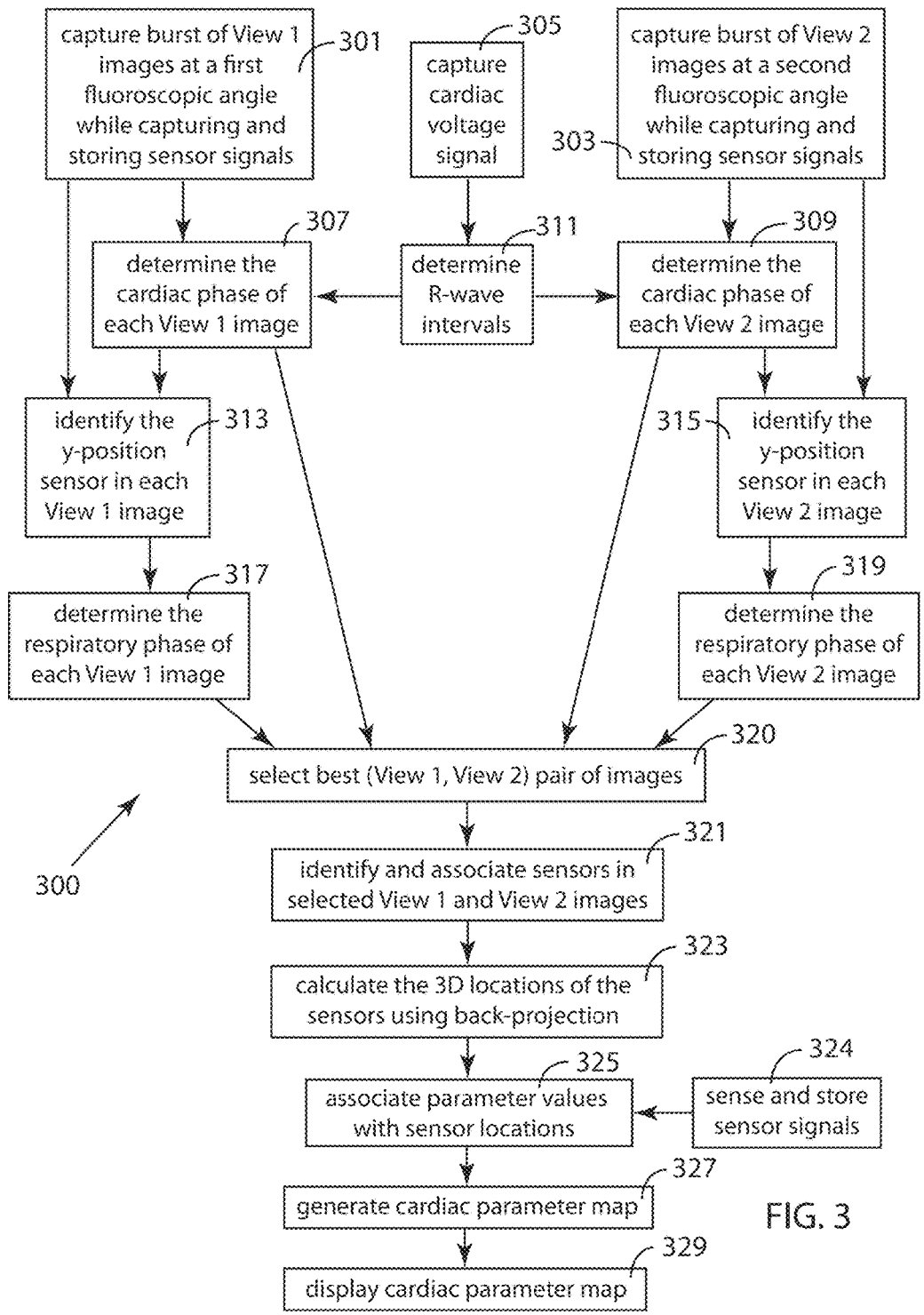
FIG. 3 is a schematic block diagram illustrating an embodiment of the inventive method for rapidly generating a 3D map of a cardiac parameter in a region of a living heart into which region a plurality of radio-opaque sensors has been placed, the method using single-plane fluoroscopic images. In the exemplary method presented in FIG. 3 and following, the sensors are cardiac electrodes measuring voltages, and the cardiac parameter map is a local activation time (LAT) map.
Figures 1, 4:
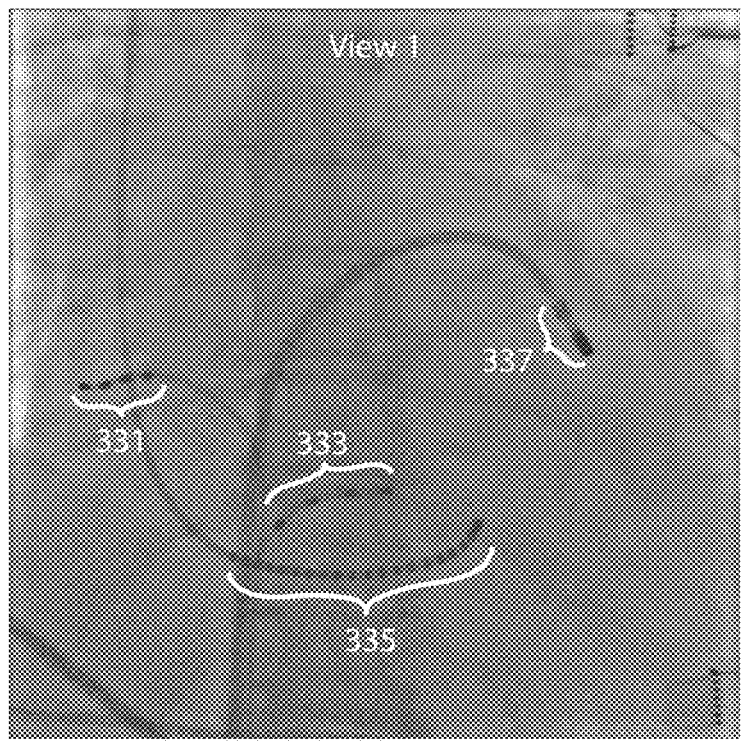
Figures 2, 4:
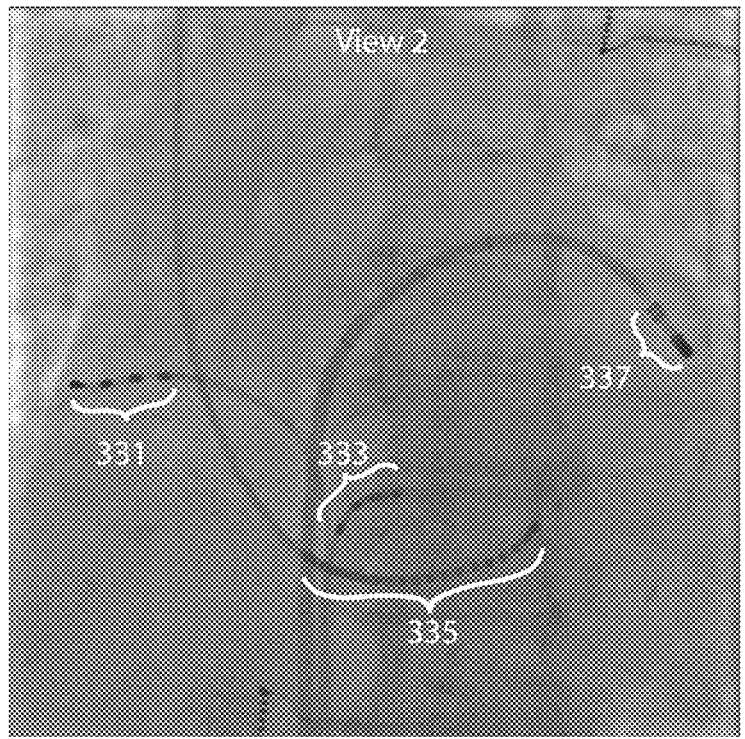

When the present invention is applied within C3DLS 20 as part of the steps in initialization/calibration 21, in addition to determining the parameters measured in method steps 39, 41A and 41B, View 1 images from a first fluoroscopic angle and View 2 images from a second fluoroscopic angle which is different from the first angle, may be captured with such images including a plurality of sensors (e.g., cardiac electrodes 331-337, see FIGS. 4-1 and 4-2). These images may be used to rapidly determine initial 3D locations for such sensors, and these locations are then used to rapidly generate an initial 3D physiological-parameter map (e.g., an LAT map). Details of these inventive method steps are described in FIG. 3 and following and their accompanying descriptive text.

FIG. 3 is a schematic block diagram illustrating an embodiment 300 of the inventive method for rapidly generating a 3D map of a cardiac parameter in a region of a living heart into which region a plurality of catheters, each having one or more radio-opaque sensors, has been placed. The method uses single-plane fluoroscopic images taken from two different angles (View 1 and View 2) in order to enable calculation of the 3D locations of the sensors. In the exemplary method presented herein, the sensors are cardiac electrodes measuring voltages, and the parameter map is a local activation time (LAT) map. The inventive method involves the use of one or more programmable computers to carry out the image processing, signal processing and other computational steps involved. In addition to the plurality of sensors, apparatus to sense cardiac rhythm, such as an R-wave detector with its associated electrodes, may be required to supply a signal from which the cardiac phase of the single-plane fluoroscopic images may be derived.

View 1 and View 2 images may be captured simultaneously (with first and second fluoroscopes) or sequentially (with a single fluoroscope set at a first angle and then subsequently at a second angle). In embodiment 300, a single fluoroscope is used first to capture a burst of View 1 images in method step 301 and subsequently to capture a burst of View 2 images (at a second angle, different from the first angle) in method step 303. (In the example which follows, the frame rate of the fluoroscope is 15 frames/second.) The time period of the bursts should be long enough to incorporate at least one full respiratory cycle.

In steps 301 and 303, while the fluoroscope is capturing images, the sensors which have been placed within a region of the living heart may be sensing the cardiac parameter to be mapped with such sensed parameter data stored for later use. The sensing and storing of the physiological data may also occur at other times (e.g., in method step 324); contemporaneous imaging and sensing in steps 301 and 303 is not intended to be limiting. As long as the sensors remain at their determined 3D locations relative to the structure of the heart, later-sensed physiological data are useful to be associated with the corresponding sensors.

In method step 305, a cardiac voltage signal is captured from which R-wave intervals may be determined in method step 311. Functional elements 307 and 309 use the R-wave data from step 311 to determine a cardiac phase for each View 1 image (step 307) and View 2 image (step 309).

In the inventive method, cardiac phase and respiratory phase information are utilized to select the best View 1 and View 2 images for 3D location determination. Since patient motion during a cardiac procedure is primarily caused by cardiac and respiratory activity, in order for sequential View 1 and View 2 images to be used for a calculation which ideally employs image data taken at the same instant in time, selecting the best or optimal View 1 and View 2 images involves finding the pair of images for which a combination of differences in both motion phases is a minimum. Thus, method step 307 and 309 determine cardiac phase information for each View 1 and View 2 images, respectively.

Method steps 313 and 315 (View 1 and View 2, respectively) comprise the identification of one of the plurality of sensors as the source of displacement information from which respiratory phase information may be determined. Since motion of objects in the y-direction in a sequence of images (generally parallel to the patient's spine) is primarily the result of respiratory motion, the y-coordinate of an object in a burst (sequence) of images may be used to estimate respiratory phase. In the example which is illustrated below, the smallest y-position value is closest to full exhalation.

Initial identification of a y-position sensor 337 (see FIGS. 4-1 and 4-2) may be done manually on a computer display within the first image in each of the View 1 and View 2 bursts of images. Then the motion of y-position sensor 337 is determined within each image of the burst in order to determine respiratory phase information for each image in the burst. Y-position sensor 337 may be the same sensor in each of the View 1 and View 2 bursts of images, but it is not necessary that this be so since all that is required is the y-positions within each burst be indicative of the respiratory movement of a sensor within the burst. The fact that in embodiment 300 the sensor is the same in both bursts is not intended to be limiting. Furthermore, it is not necessary that the object being used to sense y-position be a sensor; any intra-cardiac radio-opaque object in the field of a burst may provide the necessary y-position information; the use of a sensor for y-position determination is not intended to be limiting.

The y-coordinate of y-position sensor 337 is that of the geometric center of the image of sensor 337, and such determination is well-known to those skilled in image processing. The coordinates of all sensors in the View 1 and View 2 images are also determined in this fashion. Use of the geometric center for such determinations is not intended to be limiting.

Method steps 317 and 319 comprise determination of the respiratory phase of each image in the View 1 and View 2 bursts, respectively. One embodiment of such determination is exemplified in detail in FIGS. 4-1 through 8-2.

Figures 1, 8:
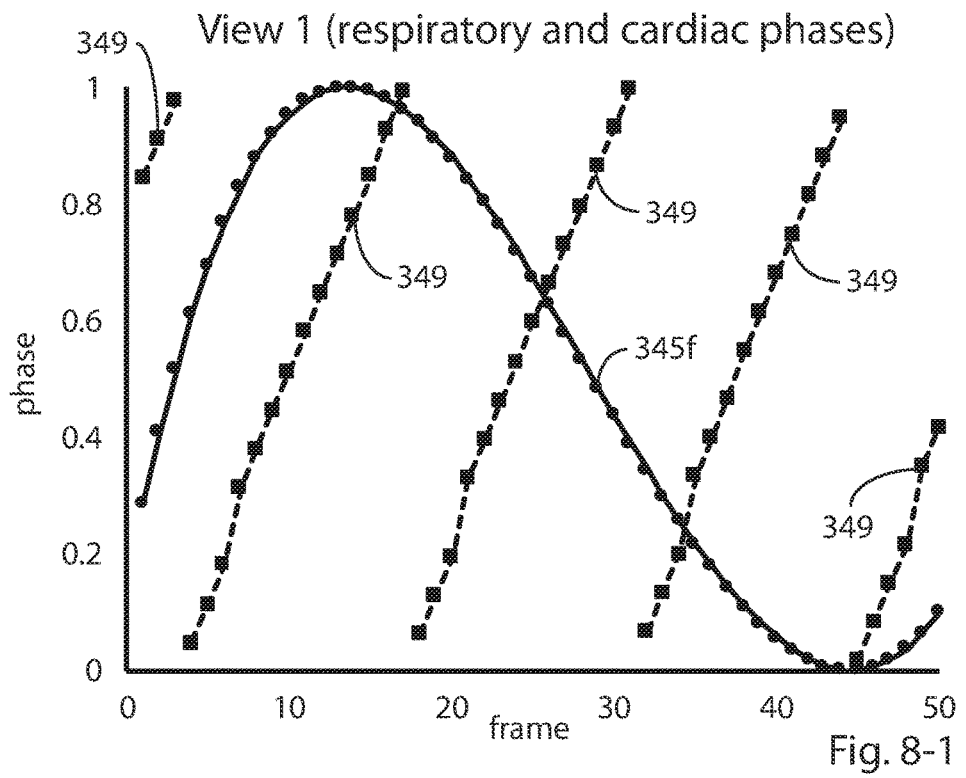

Functional element 320 comprises method steps by which a best View 1 image and a best View 2 image are selected to minimize the effects of cardiac and respiratory motion within the subsequent calculations of the 3D locations of sensors 331-337. One embodiment of method step 320 is illustrated in FIGS. 8-1 through 27.

After best View 1 and View 2 images have been selected in method step 320, method step 321 comprises the identification within such images of each sensor 331-337 for which 3D location is to be determined. Method step 321 further comprises associating each such sensor in the best View 1 image with its corresponding sensor in the best View 2 image. Such associating of sensors between the best View 1 and View 2 images may be done manually by user interaction with display 14.

In functional element 323, back-projection calculations are used to determine the 3D locations of sensors 331-337. Since the determination of the coordinates of sensors 331-337 in the View 1 and View 2 images is affected by several noise sources, a least-squares approach for the back-projection calculations may be used to determine the best estimates of such 3D locations. The mathematics involved in the back-projection method, including the use of a least-squares solution, is well-known to those skilled in mathematics.

With the 3D locations of sensors 311-337 determined in method step 323, cardiac parameter data from sensors 331-337 is associated with the 3D locations of sensors 331-377 in method step 325, and in subsequent method steps the parameter values and 3D locations are used to generate (step 327) and display (step 329) a map of the cardiac parameter. As long as sensors 331-337 remain at the same 3D locations relative to cardiac structure, cardiac parameter data captured in method step 324 can subsequently be mapped.

The method described above and illustrated in the figures and discussion which follow essentially determines 3D sensor locations and captures, processes and stores data from the sensors such that the multiple map points with associated cardiac parameter values are simultaneously (in parallel) generated, providing extremely rapid initial mapping with very low X-ray exposure. After the 3D locations have been determined, if the relative positions of the sensors within the heart do not change, the simultaneous updating of sensor data provides parallel, nearly instantaneous updating of the cardiac parameter map.

FIG. 4-1 shows a representative View 1 X-ray image of a patient's chest taken at a first fluoroscope angle, in this case in an anterior/posterior (AP) orientation one (1) degree toward the left. FIG. 4-2 shows a representative View 2 X-ray image of the same patient taken at a second fluoroscope angle, in this case in a left anterior oblique orientation twenty (20) degrees to the left. The patient is lying on his back with X-ray source 11 underneath him and X-ray detector 13 above his chest. C-arm 8 of conventional fluoroscope 10 has been rotated 19 degrees around the y-axis (parallel to the patient's spine) to change from View 1 to View 2.

It has been found that an angle difference of about 20 to 30 degrees provides a suitable pair of fluoroscopic angles. Angle differences which are too small cause trigonometric errors in subsequent back-projection calculations, and angle differences which are too large introduce errors due to differences in the sag in the gantry of fluoroscope 10 between the first and second fluoroscope angles.

Sensors 331-337 are cardiac electrodes, as follows: sensors 331 are two pairs of bipolar electrodes on the end of a high right atrium catheter; sensors 333 are two pairs of bipolar electrodes on the end of a bundle of His catheter; sensors 335 are ten pairs of bipolar electrodes on the end of a coronary sinus catheter; and sensors 337 are two pairs of bipolar electrodes at the end of a mapping/ablation catheter. The sensor 337 at the distal end of the mapping/ablation catheter includes both electrodes and apparatus for ablating cardiac tissue while the sensor 337 above and to the left of the distal end is a pair of electrodes called the proximal rings.

Although the number of sensors shown in FIGS. 4-1 and 4-2 (and FIGS. 11-1 and 11-2) are quite modest, it is anticipated that the number of sensors being 3D-located with the inventive method and subsequently used to generate a 3D parameter map) may be as high as 256. Such number of sensors is, however, not intended to be limiting.

Figure 5:
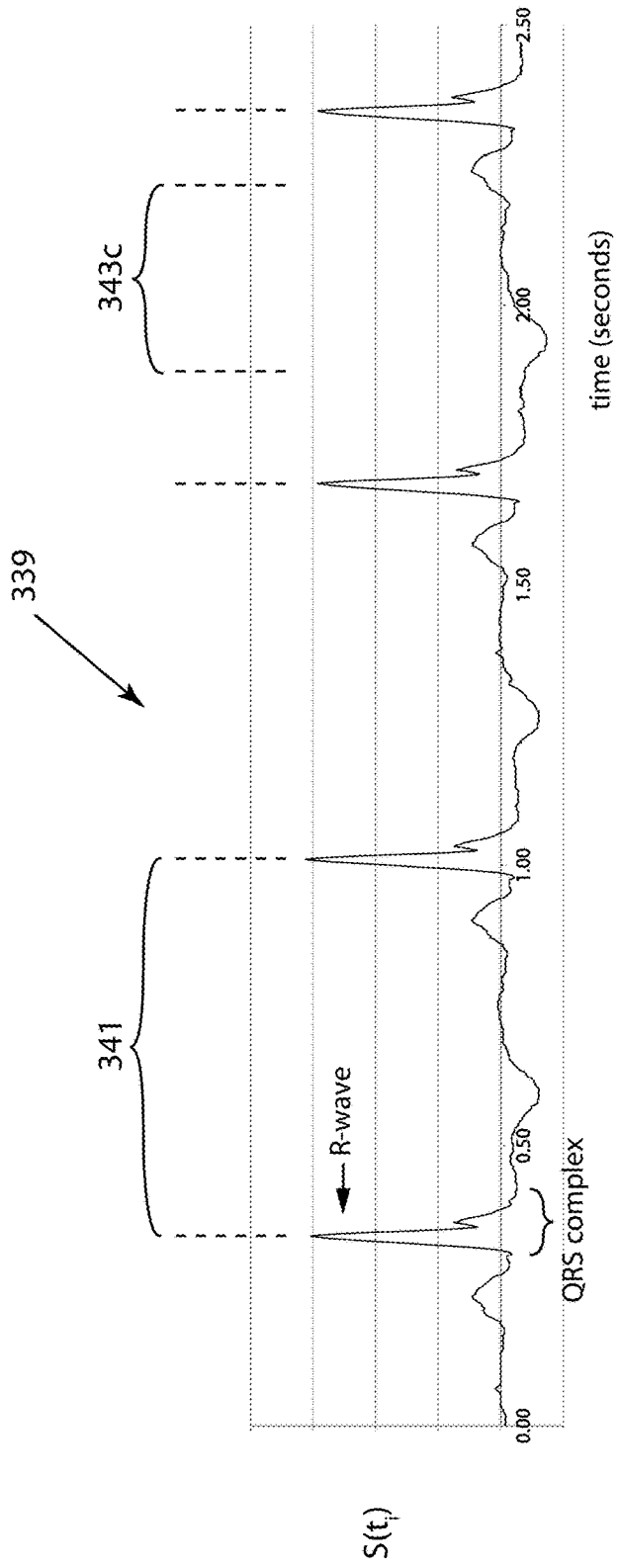
FIG. 5 is an exemplary time plot of a digitized signal $S(t_i)$ from an R-wave detector. The signal is used to derive cardiac phase information for each View 1 and View 2 image.

FIG. 5 is an exemplary time plot 339 of a digitized signal $S(t_i)$ from an R-wave detector. Signal $S(t_i)$ is used to derive cardiac phase information for each View 1 and View 2 image. R-wave intervals 341 are the time periods (cardiac cycle lengths) between neighboring R-waves from the QRS complexes within signal $S(t_i)$. X-ray frames are captured sequentially, each occurring at some time relative to an R-wave interval 341, and based on the position in time within R-wave interval 341, a value of cardiac phase is assigned to each View 1 and View 2 image. As mentioned above, it is beneficial to determine 3D sensor location using a pair of View 1 and View 2 images taken during periods of minimal cardiac and respiratory motion. As part of this determination in method step 320, a cardiac-phase criterion 343c (as shown in FIG. 5, frames with cardiac phase between 30% and 80% of R-wave interval 341) are frames which satisfy such a cardiac-phase criterion 343c (0.3 cardiac phase 0.8). This 30%-80% value of cardiac phase criterion 343c is not intended to be limiting; values outside this range may also be used.

Figures 1, 6:
Figures 1, 7:
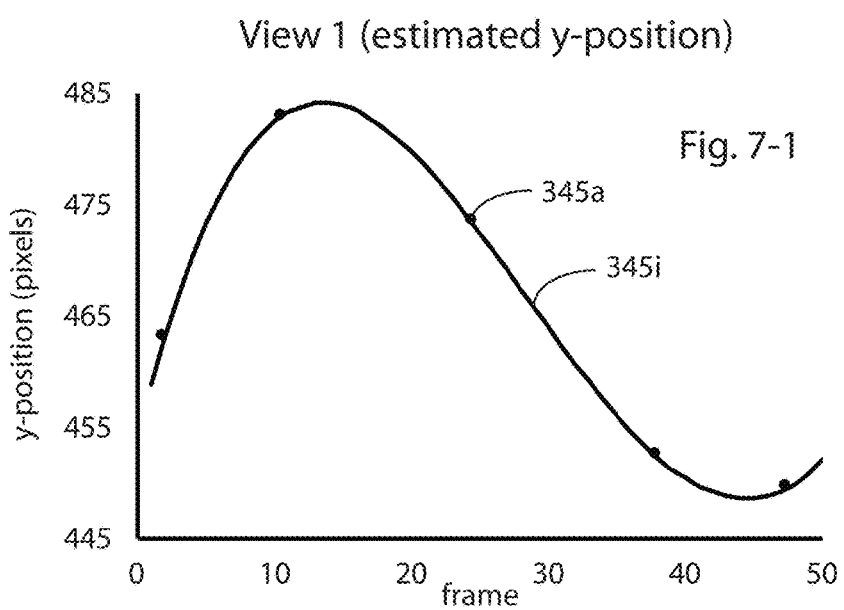

The respiratory phase of View 1 and View 2 images is determined from changes from frame-to-frame in the y-positions of sensor 337 in method steps 317 and 319, respectively. FIGS. 6-1 and 6-2 are plots of exemplary y-position data for sensor 337 in the fifty View 1 (data points along line 345) and fifty View 2 (data points along line 347) images, respectively. Given the nature of such data, an estimate of respiratory phase is made, and FIGS. 7-1 and 7-2 are plots of the y-position data of FIGS. 6-1 and 6-2, respectively, which has been smoothed (points 345a and points 347a, respectively) and interpolated (line 345i and line 347i, respectively) to generate an estimate of respiratory phases for View 1 and View 2 images.

Several alternative approaches are possible for such smoothing and interpolation. In this example, each of the View 1 frames occurs during some portion of five different R-wave intervals, and each of the View 2 frames occurs during some portion of another five different R-wave intervals. Each point 345a and 347a is calculated by averaging the y-positions from the frames within each R-wave interval and averaging the corresponding frame numbers to generate highly-smoothed representations of respiratory phase across the View 1 and View 2 sets of frames. Curves 345i and 347i are generated by computing a cubic-spline fit to these sets of points 345a and 347a, respectively, to yield estimates of respiratory phase for each image.

FIGS. 8-1 and 8-2 are plots which present both the respiratory and cardiac phases for each of the fifty View 1 frames and fifty View 2 frames, respectively. The values of both the cardiac phase and respiratory phase have been normalized onto 0-1 scales. In FIGS. 8-1, 8-2, 9-1 and 9-2, cardiac phase values for the frames are shown with small square marks, and respiratory phase values are shown with small circular marks. The solid and dotted lines are shown only for ease of viewing. In FIGS. 8-1 and 8-2, each dotted-line group of marks 349 (View 1) and 355 (View 2) represent the cardiac phase of frames occurring within a specific R-wave interval 341. Note that in FIG. 8-1, there is a larger vertical gap between marks around cardiac phase of about 0.25 (and in FIG. 8-2, around cardiac phase 0.5). These "anomalies" in the data are the result of a setting on the particular fluoroscopic system 10 which captured these images which purposely dropped every $14^{th}$ frame. This setting causes no substantive difference in the steps of the method directed toward selecting the best pair of View 1 and View 2 images for calculation of 3D locations of sensors (electrodes) 331-337.

Figures 1, 9:
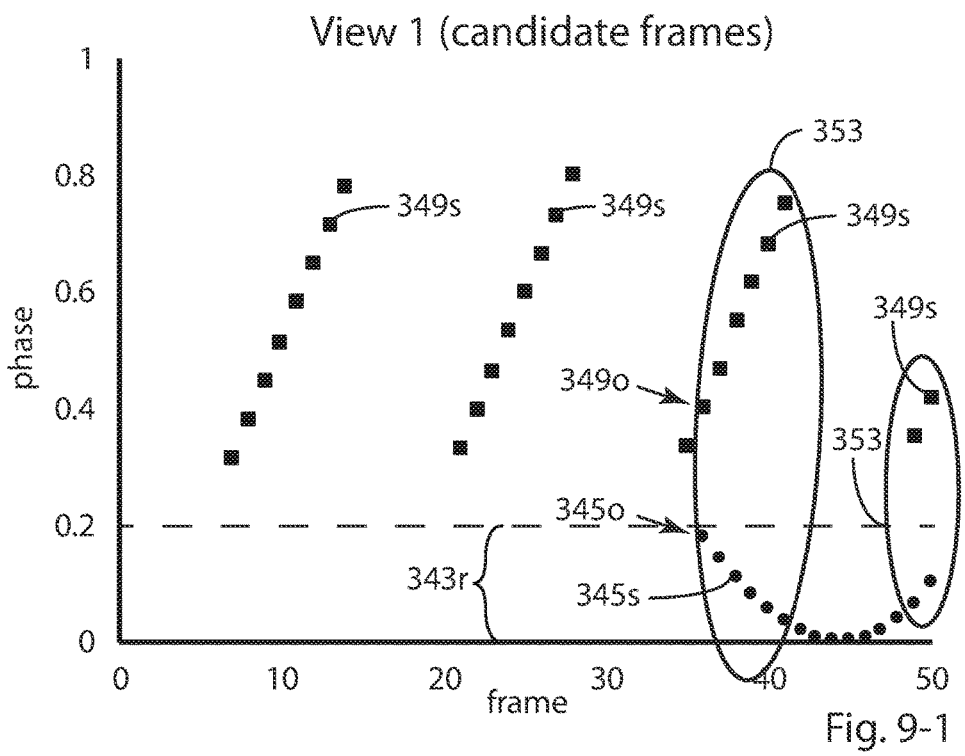
Figures 2, 8:
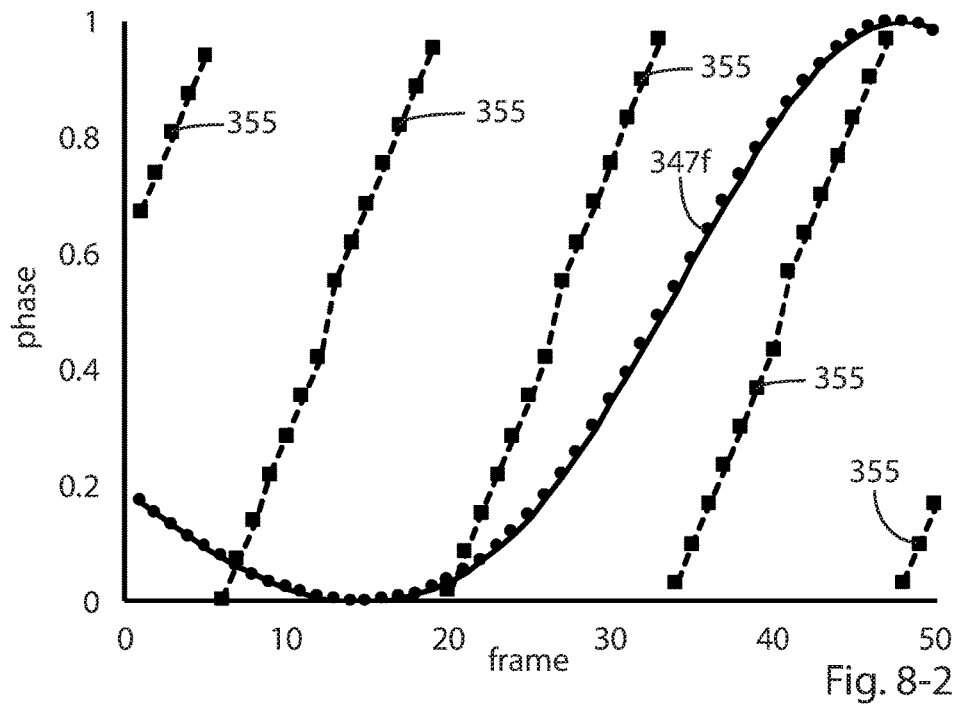
Figures 2, 9:
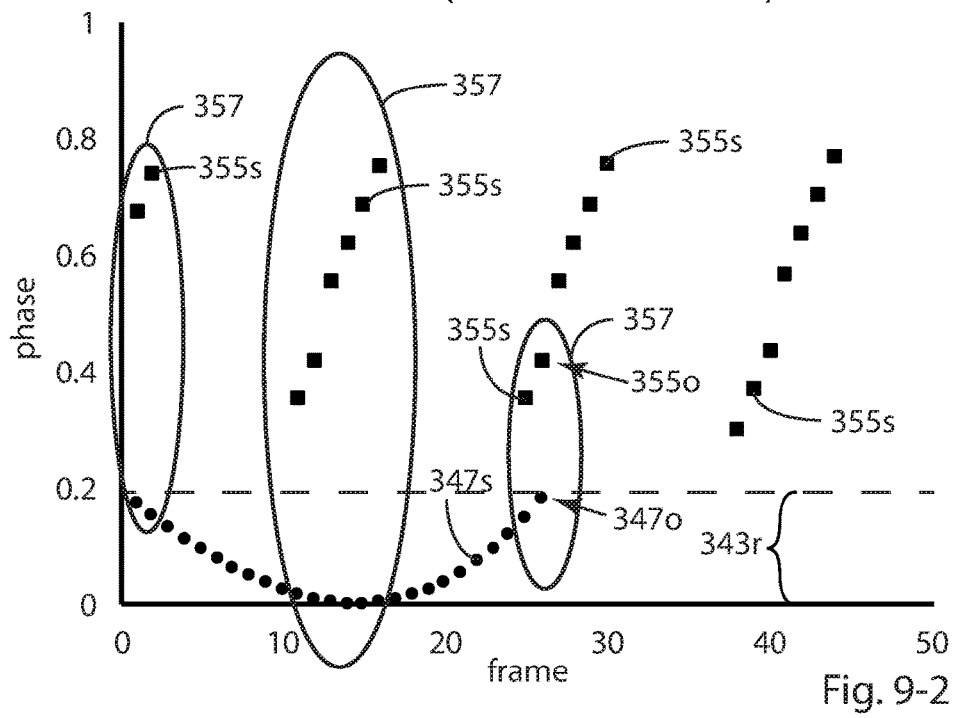

FIG. 9-1 presents plots of View 1 frames 349s which satisfy cardiac-phase criterion 343c and frames 345s which satisfy a respiratory-phase criterion 343r. FIG. 9-2 presents plots of View 2 frames 355s which satisfy cardiac-phase criterion 343c and frames 347s which satisfy respiratory-phase criterion 343r. In this example, respiratory-phase criterion 343r is such that frames which satisfy the criterion have a respiratory phase between 0% and 20% of maximum exhalation (respiratory phase 0.2). FIGS. 9-1 and 9-2 therefore show cardiac phase and respiratory phase for a subset of the frames shown in FIGS. 8-1 and 8-2.

Final selection of the best View 1 and View 2 images therefore is reduced to selecting from among the View 1 and View 2 images which satisfy both the cardiac-phase criterion 343c and respiratory-phase criterion 343r. These include View 1 images for which the cardiac phase and respiratory phase values fall within the two regions 353, and View 2 images for which the cardiac phase and respiratory phase values fall within the three regions 357. The candidate View 1 images $I_i$ are frames 36-41 and 49-50, and the candidate View 2 images $I_j$ are frames 1-2, 11-16 and 25-26.

Figure 10:
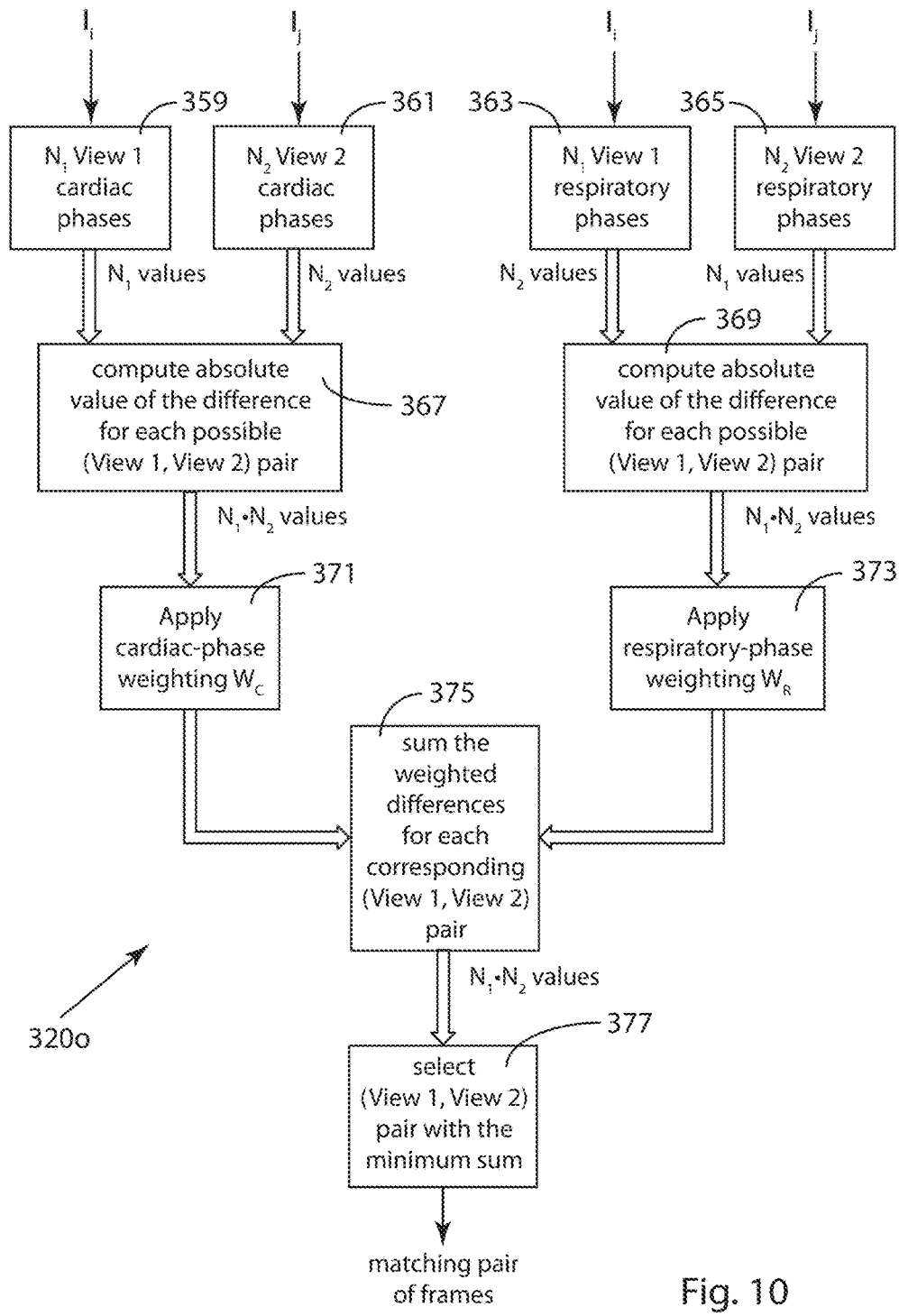
FIG. 10 is a schematic block diagram illustrating an embodiment of the method of selecting the best View 1 and View 2 frames from the sets of candidate View 1 and View 2 frames.

FIG. 10 is a schematic block diagram illustrating an embodiment 320o of the final selection of the best View 1 and View 2 frames from the sets of candidate View 1 frames within regions 353 and candidate View 2 frames within regions 357. As indicated in FIG. 10, in this example there are $N_1$ View 1 frames $I_i$ ($N_1$=8; index i=1 to 8) and $N_2$ View 2 frames ($N_2$=10; index j=1 to 10).

In FIG. 10, method steps 359, 361, 363 and 365 represent the fact that calculations within the method steps 320o are made using the cardiac phase and respiratory phase values of View 1 frames $I_i$ and View 2 frames $I_j$ as illustrated in FIGS. 9-1 (View 1) and 9-2 (View 2). In method step 367, the absolute values of the differences between the cardiac phases of all possible pairs of $N_1$ View 1 frames $I_j$ and $N_2$ View 2 frames $I_j$ are computed; there are $N_1 \cdot N_2$ such pairs and absolute difference values. Similarly, in method step 369, $N_1 \cdot N_2$ absolute difference values for the respiratory phases are computed. In functional element 371, each of the $N_1 \cdot N_2$ values cardiac-phase differences is multiplied by cardiac weighting $W_C$, and in similar fashion, in method step 373 the $N_1 \cdot N_2$ respiratory-phase differences are each multiplied by respiratory weighting $W_R$. (In the specific example illustrated in FIGS. 4-1 through 9-2, values of $W_C$=1 and $W_R$=1 are used.)

In method step 375, the corresponding pairs of $N_1 \cdot N_2$ cardiac-phase differences and $N_1 \cdot N_2$ respiratory-phase differences are summed to generate a set of $N_1 \cdot N_2$ values, and in method step 377, the minimum value in this set is selected as the "best" or "matching" pair of View 1 and View 2 frames. The weighted sum formed for each pair of frames in method step 375 is one possible measure of the similarity of the View 1 and View 2 frames in each pair of frames, and the similarity criterion is that such measure is to be minimized.

Similarity can be thought of as the reciprocal of this measure since smaller values of such measure represent greater frame-to-frame similarity. In other words, the minimum value of the sum among the $N_1 \cdot N_2$ values computed in method step 375 represents the maximum similarity (minimum combined phase differences) among the pairs of candidate frames. The result of the method steps 320o of FIG. 10 is that View 1 frame number 36 and View 2 frame number 26 are selected as the best or matching pair of frames. In FIG. 9-1, View 1 frame 36 is labeled with reference numbers 349o (cardiac phase) and 345o (respiratory phase). In FIG. 9-2, View 2 frame 26 is labeled with reference numbers 355o (cardiac phase) and 347o (respiratory phase).

Figures 1, 11:
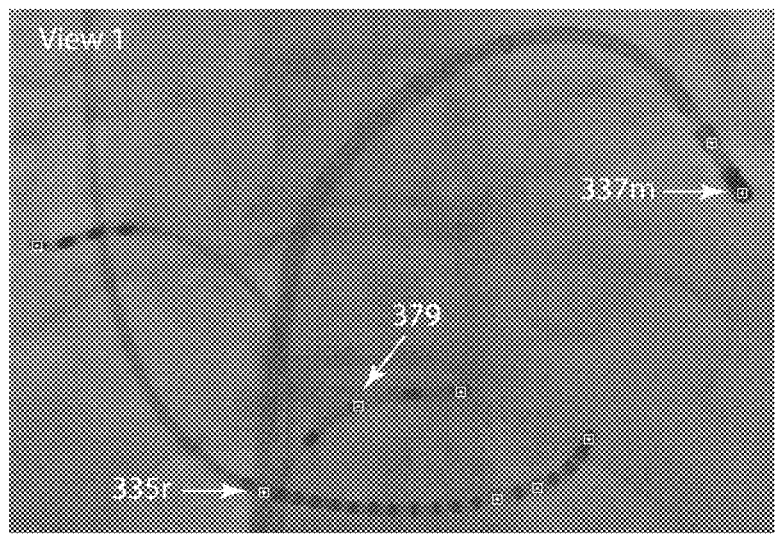
Figures 2, 11:
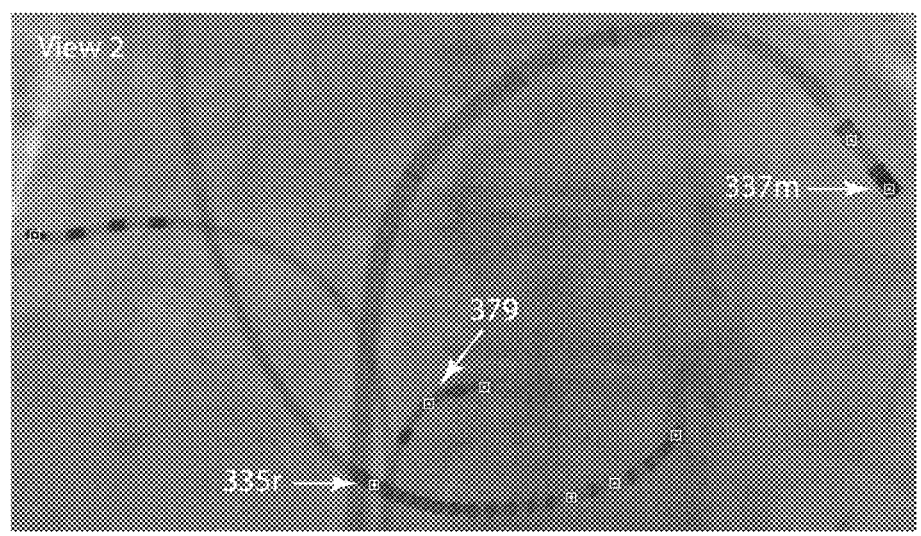

FIGS. 11-1 and 11-2 are portions of the same X-ray images as in FIGS. 4-1 (View 1 frame 36) and 4-2 (View 2 frame 26), respectively, with a subset 379 of the electrodes identified and then associated with the corresponding electrodes in the selected View 1 and View 2 images. (Only the regions of such images which contain cardiac catheter electrodes 331-337 are shown.) Electrodes in subset 379 have been chosen based on the efficacy of the signals from electrodes 331-337. Cardiac electrodes 331-337 which are in satisfactory contact with live cardiac muscle tissue will produce a useful signal. Thus, only subset 379 of electrodes have suitable signals from which to compute LAT values in the example. Only three arrows point to the electrodes in subset 379 to simplify the images. In the example, the reference electrode used for the LAT computations is shown as electrode 335r, and reference electrode 335r and the mapping sensor electrode 337m at the distal end of the mapping/ablation catheter are also electrodes in subset 379.

Note that only one cardiac electrode in each bipolar pair is identified and associated with its corresponding electrode in the pair of View 1 and View 2 frames. FIGS. 11-1 and 11-2 therefore show nine identified and associated electrodes. The correspondence between sensors 331-337 and the electrodes in subset 379 is easily seen by comparing FIGS. 11-1 and 11-2 with FIGS. 4-1 and 4-2. It is the 3D locations of the electrodes in subset 379 along with the computed LAT (cardiac parameter) values associated with the electrodes of subset 379 which are used to generate an LAT map as described below.

Referring again to FIG. 3, the generation and display of a 3D map of a cardiac parameter occur within method steps 327 and 329, respectively. As noted above, the region of the heart being 3D-mapped may be planar or volumetric. Although the region of the heart is typically a volume, planar regions are also of medical importance. When the region is planar (all sensors lie in a single plane), the parameter values associated with intermediate points within the map plane are simply determined by linear interpolation of the parameter values associated with the 3D-located sensors. As noted herein above, the resulting parameter map is considered to be a 3D map since its three-dimensional location and orientation constitute important information generated by the inventive method. Parameter maps of both planar and volumetric regions are displayed in the same way using 3D display technology so that all of the 3D information contained in the maps is available to be viewed.

Figure 12:
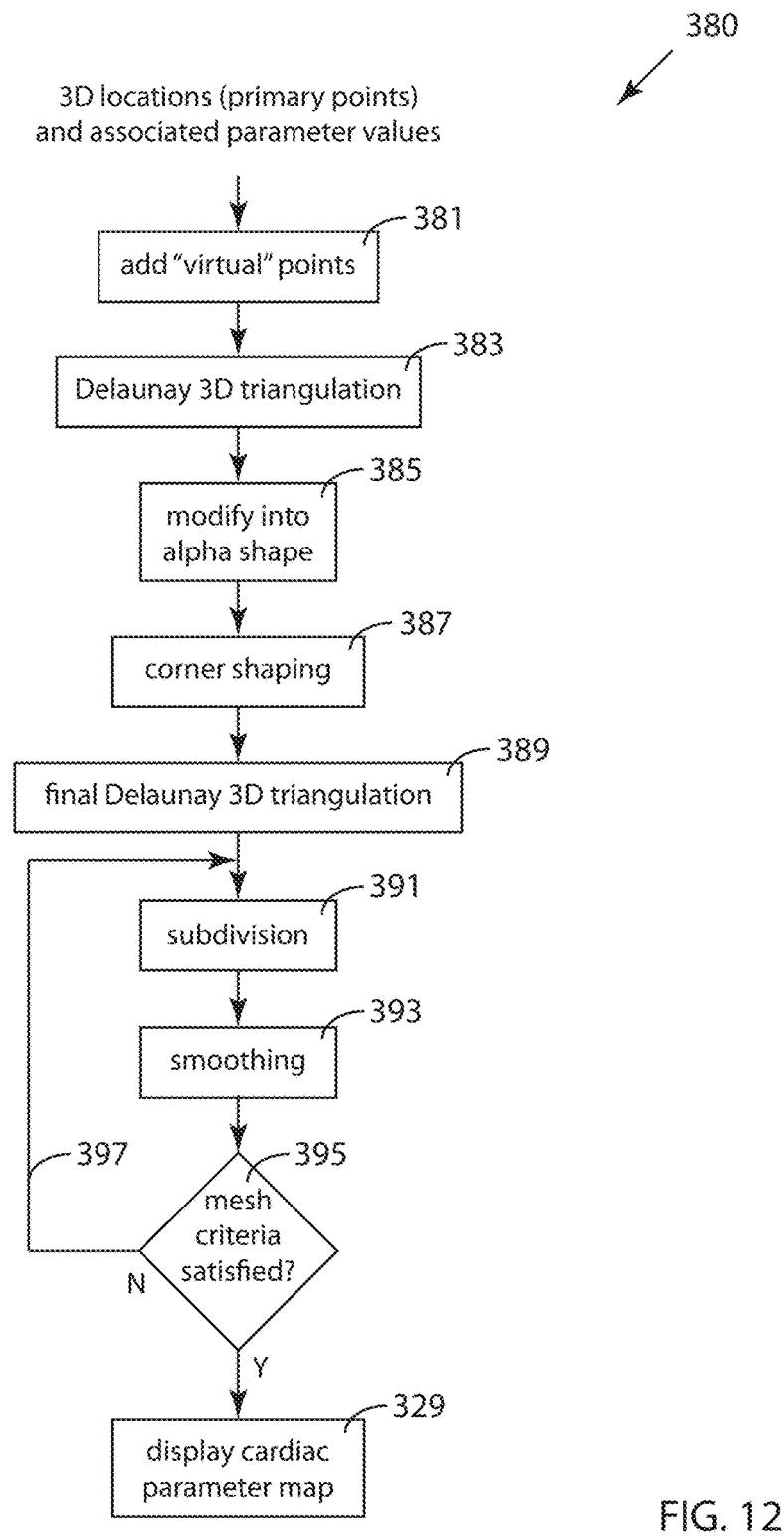
FIG. 12 is a schematic block diagram illustrating one embodiment by which a cardiac parameter map which spans a volumetric region of the heart may be generated and displayed based on determined 3D locations of a plurality of sensors and sensed cardiac parameter values.

When the region is a volume (at least four non-coplanar sensors), a surface reconstruction process may be employed in order to generate the 3D parameter map. One embodiment 380 of a surface-reconstruction method for generating 327 and displaying 329 such a cardiac parameter map is illustrated in the schematic block diagram of FIG. 12. In method step 381, starting with the 3D sensor locations (primary points) determined by back-projection calculations 323, "virtual" points are added around one or more of the primary points in order to be able to generate a stable mesh in the next step of the process. This is particularly important when the number of primary points is small. The cardiac parameter values assigned to these "virtual" points are the values associated with the primary-mesh point near to the added "virtual" points.

In method step 383, a primary mesh is formed by performing Delaunay 3D triangulation to create a triangulated volume which only includes the primary points and the virtual points added in method step 381. In method step 385, the primary mesh is modified into an alpha shape, employing a value of alpha large enough to produce a closed surface.

In method step 387, the primary mesh is further modified by shaping (rounding off) sharp corners by augmenting corners with more points in order to satisfy a local angle criterion. In method step 389, the modified primary mesh is regenerated by applying a final Delaunay 3D triangulation process to create a final primary mesh which incorporates the effect of the points added for corner-shaping. Values of the cardiac parameter associated with points in the final primary mesh are determined by linear interpolation.

The primary mesh is then subdivided (adding more points and smaller intervening surfaces) in order to produce a more accurate surface which has all mesh points close to such surface. Method steps 391 through 395 and loop path 397 together comprise an iterative mesh-smoothing process which enables the final primary mesh to appear more natural (more like a physiological structure). In method step 391, additional intermediate mesh points are added to the primary mesh by a process of subdivision, and the resulting mesh is smoothed in method step 393. Laplacian and cotangent smoothing are among the smoothing approaches which may be applied in smoothing step 393. In decision step 395, the mesh is tested against smoothing criteria to determine if the mesh has nearly uniform edges of length below a predetermined threshold. If the criteria are not satisfied, the mesh is iteratively modified by looping back along loop path 397 to subdivision method step 391 and proceeds further until the criteria are satisfied in decision step 395. Cardiac parameter values are associated with these added points on the map by distance-weighting averages of the values at the points nearest the point in question. Each of method steps in method embodiment 380 is based on procedures well-known to those skilled in the area of surface reconstruction.

When the mesh criteria are satisfied and surface reconstruction is complete, in method step 329 (see FIG. 3), the cardiac parameter map is displayed for a user on a visual display.

Figure 13A:
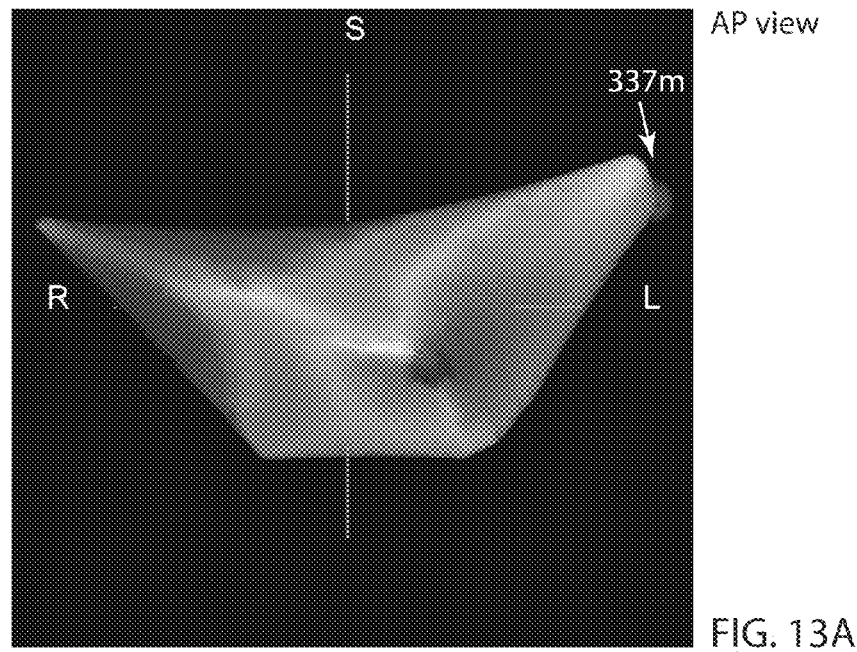
FIGS. 13A through 13C are three views of an exemplary LAT map derived from the data captured in the example of FIGS. 4-1 through 11-2.
Figure 13B:
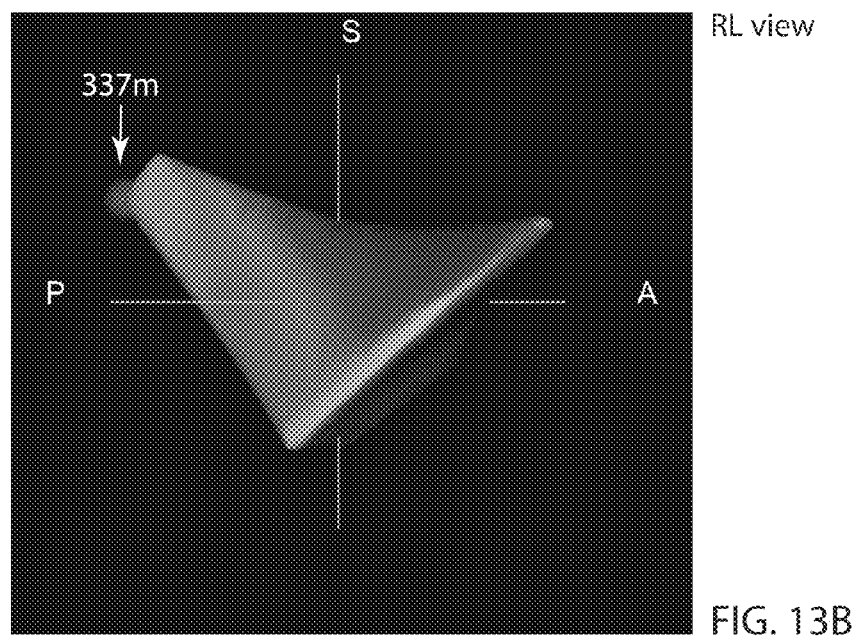
Figure 13C:
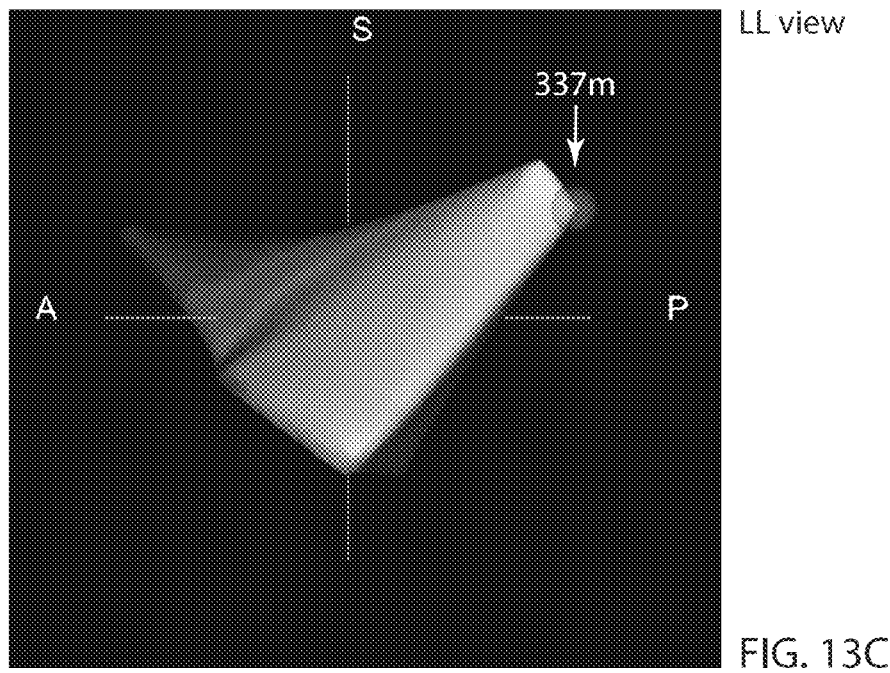

FIGS. 13A through 13C are three views of an exemplary LAT map derived from the data captured in the example of FIGS. 4-1 through 11-2. Referring again to FIG. 3, data used for the generation of the LAT maps in FIGS. 13A-13C were captured and stored in method step 324 subsequent to the selection 320 of the best View 1 and View 2 images. The LAT map view in a FIG. 13A is an anterior/posterior view of the exemplary LAT map; FIG. 13B shows a right lateral (RL) view; and FIG. 13C shows a left lateral (LL) view.

In the LAT map views in FIGS. 13A-13C (and FIG. 16), the location of mapping electrode 337m is indicated by the purple spherical region surrounding mapping electrode 337m. FIGS. 13A-13C (and FIG. 16) also include markings with the letters which mean the following: A (anterior); P (posterior); R (patient right); L (patient left); and S (superior or head).

As indicated in FIGS. 13A-13C (and also in FIG. 16), the average cardiac cycle length is 259 ms (milliseconds), and the LAT data displayed range from −52 ms to +70 ms relative to the occurrence of a cardiac signal fiducial (passage of a depolarization wave) in the signal captured from reference electrode 335r. Methods for the computation of LAT values and the importance of cardiac signal fiducials in such LAT computations are well-known to those skilled in the area of signal processing and/or electrocardiology. FIG. 13A through FIG. 16 include a color bar CB which indicates the LAT values on the maps as the color spectrum (red to magenta) varies linearly along color bar CB between −52 ms and +70 ms.

Figure 14:
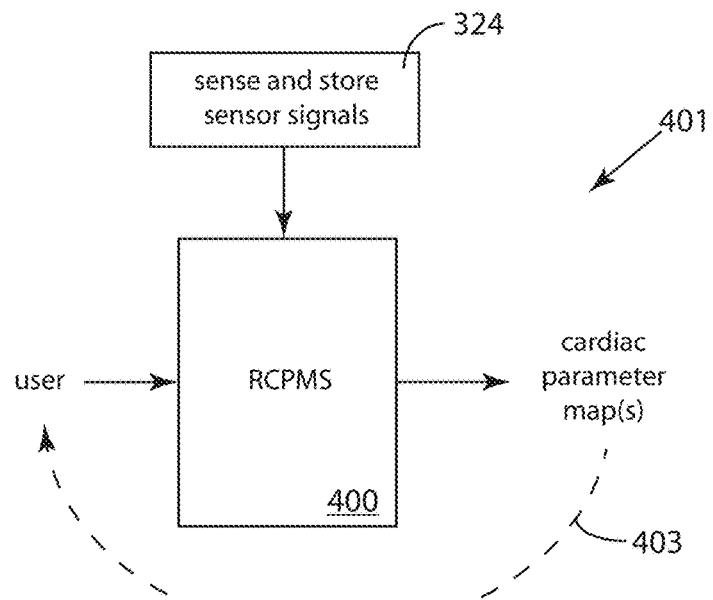
FIG. 14 is a simple block diagram schematic of an embodiment of the inventive method for rapid cardiac parameter mapping such as the generation of additional maps based on input from a user.
Figure 15:
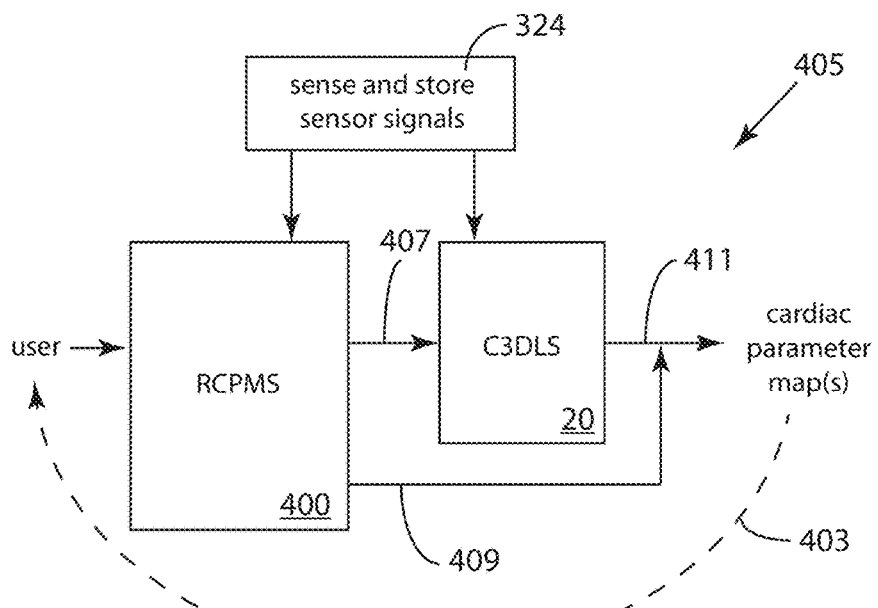
FIG. 15 is a simple block diagram illustrating the cooperative use of the inventive method of FIG. 3 as a portion of the initialization steps of C3DLS.

The user is able to interact with the display at least as illustrated in FIGS. 14 and 15 and described in the following section. FIG. 14 is a simple block diagram schematic of an embodiment 401 illustrating some additional features of the inventive method for rapid cardiac parameter mapping such as the generation of additional maps based on input from a user. For convenience, the inventive method for rapid cardiac parameter mapping is referred to as RCPMS 400. In embodiment 401, method step 324 is shown separately to indicate explicitly that sensing and storing of cardiac parameter data to be associated with the 3D location data continues after 3D location information has been determined within RCPMS 400. The user is able to provide inputs to RCPMS 400 to trigger the generation of one or more additional maps or change an input value for a map which causes it to change. For example, since a user is viewing displayed information from RCPMS 400, the user may request that RCPMS 400 display a new parameter map using the 3D sensor locations previously determined and updated cardiac parameter values as sensed in method step 324. These observations and subsequent inputs by the user are illustrated by a dotted-line feedback pathway 403.

In situations where the sensors are cardiac electrodes and the parameter being displayed is local activation time (LAT) based on a reference signal from one of the cardiac electrodes, the user may request the display of a new LAT map based on a reference signal from another of the plurality of electrodes. Or the user may request that RCPMS 400 display more than one such map contemporaneously. Further, the user may request that the LAT map being displayed be based on data within a stored cardiac cycle. Referring to FIG. 3, data sensed and stored in method steps 301, 303 and 324 are available for map generation and display at times after such data are captured.

FIG. 15 is a simple block diagram schematic of an embodiment 403 illustrating the cooperative use of RCPMS 400 as a portion of the initialization steps of C3DLS 20. In embodiment 403, RCPMS 400 is used to determine the 3D location of all or a portion of the plurality of sensors, and this 3D location information is provided along path 405 to C3DLS 20 which may utilize such information as it subsequently operates to determine 3D location and orientation information of a radio-opaque object using single-plane fluoroscopy from only one fluoroscopic viewing angle as described above.

In embodiment 403, method step 324 is again shown separately to indicate explicitly that sensing and storing of cardiac parameter data to be associated with the 3D location data may be generated during initialization as well as during normal operation of C3DLS 20. The computational load, data sensing, and timing requirements of both RCPMS 400 and C3DLS 20 are such that the method steps of both systems are carried out within programmable computing equipment. It is anticipated that in many instances both RCPMS 400 and C3DLS 20 may be operating within the same computing equipment and both make use of one or more computer displays driven by such computing equipment. This is illustrated in FIG. 15 by output 407 of RCPMS 400 merging with output 409 of C3DLS 20 to generate and display one or more physiological maps. As above, observation and subsequent inputs by the user are illustrated by a dotted-line feedback pathway 403.

Figure 16:
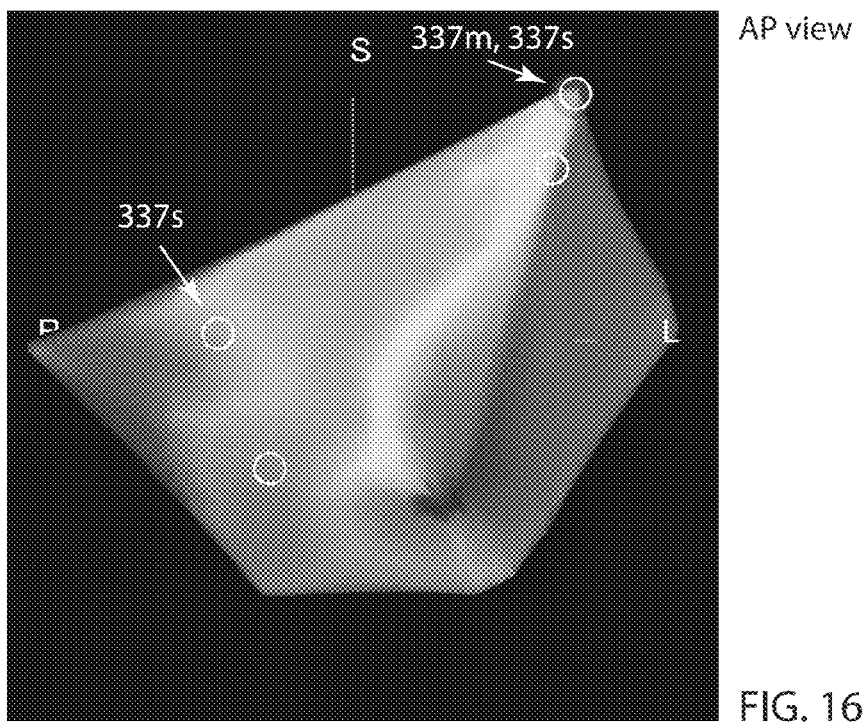
FIG. 16 is an AP view of an exemplary LAT map similar to that of FIGS. 13A-13C but with the addition of four supplemental 3D locations of a mapping sensor and their corresponding LAT values.

FIG. 16 is an exemplary LAT map similar to that of FIGS. 13A-13C but with the addition of four supplemental 3D locations of mapping electrode 337m and their corresponding LAT values. The 3D locations of the electrodes in subset 379 have been used along with four supplemental mapping points 337s established using C3DLS 20. Updated LAT values from the electrodes of the subset 379 and LAT values computed from measurements at points 337s are used to generate the map of FIG. 16. Supplemental points 337s are indicated by small white circles, only two of which have been labeled.

Comparison of the LAT map of FIG. 13A with that of FIG. 16 illustrates that the region represented by the determined 3D locations of the electrodes in subset 379 is not the entirety of a region associated with a physiological structure but is one which is enlarged by the addition of supplemental points as illustrated in FIG. 16. Nevertheless, the LAT map of FIGS. 13A-13C is of medical interest as is the LAT map of FIG. 16. The placement of sensors 331-337 at positions which are associated with known structure of the heart has enabled the extremely rapid mapping of the region, thereby dramatically reducing X-ray exposure and the length of the medical procedure, highly advantageous to a patient.

Figure 17:
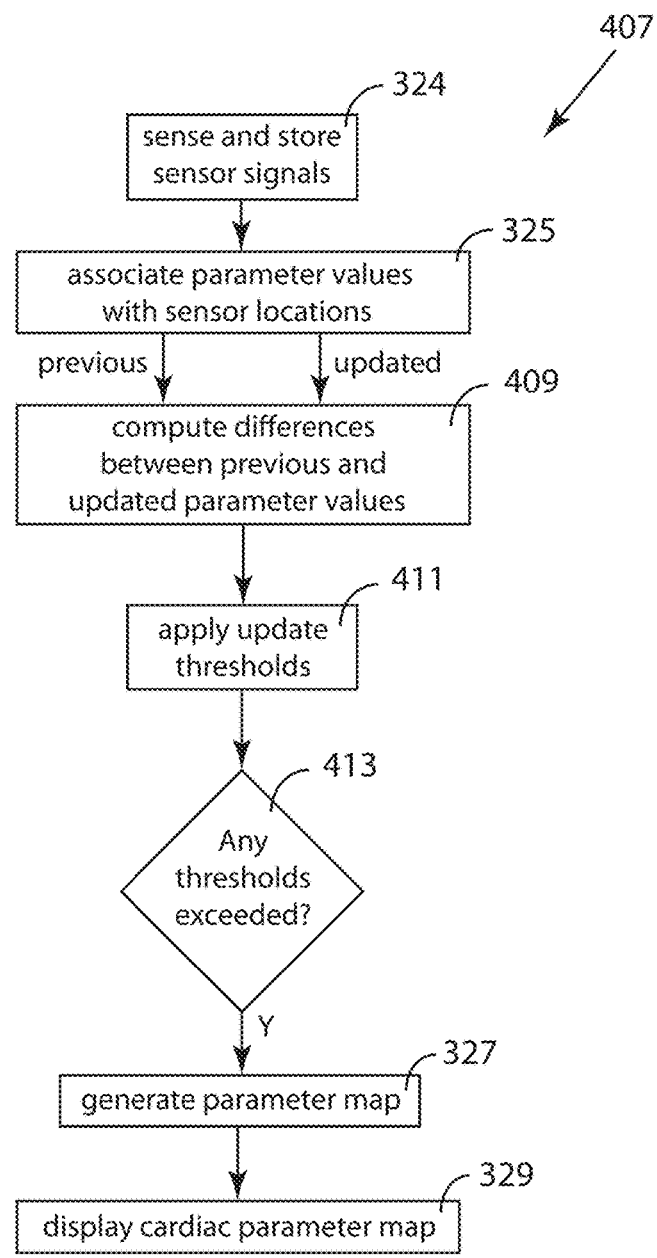
FIG. 17 is a schematic block diagram illustrating one embodiment of method steps by which the inventive method updates a cardiac parameter map based on a determination that the cardiac parameter has changed.

FIG. 17 is a schematic block diagram illustrating an embodiment 407 of method steps by which embodiment 300 of the inventive method is modified to update a cardiac parameter map based on a determination that the cardiac parameter has changed. Method embodiment 407 includes method steps 324 through 329 of method embodiment 300 in FIG. 3, but also includes the addition of method steps 409 through 413. In method step 324, as mentioned above, sensing herein refers both to the physiological measurements and to the processing of such measurements to produce the cardiac parameter if such processing is required. Method step 324 also includes storing such information for later use. Thus, not only is current (updated) cardiac parameter data available but also previous cardiac parameter data, and method step 325, as shown in embodiment 407, illustrates outputs representing the availability of both previous and updated parameter data.

In method step 409, the differences between previous and updated parameter values for each sensor in the subset are computed. Depending on the cardiac parameter being mapped, the full nature of such comparison may vary. For example, an unchanged cardiac cycle length does not indicate that a cardiac rhythm has not changed; the cycle length may not have changed while other important features of cardiac signals may change. Thus, embodiment 407 incorporates the use of differences (computed in method step 409) in each parameter value being mapped in subset 379 in order to determine whether an updated map should be generated.

In method step 411, update criteria, which in this case are update thresholds, are applied to each difference value. Update thresholds for each parameter value associated with the points in subset 379 may be different or may be the same for each parameter value. In some cases, update threshold values may be independent of the parameter values. For example, for an LAT map, update threshold may simply be a fixed number of milliseconds for each parameter value in subset 379. In other cases, it may be more appropriate to set the update thresholds to a value dependent on the parameter value itself, such as a multiple of its standard deviation (e.g., $2\sigma$). In decision method step 413, if any of the update thresholds is exceeded, an updated parameter map is generated (step 327) and may be displayed (step 329).

With a patient lying on table 12 within fluoroscopic system 10, there may be other sources of motion which affect the accuracy of the determination of the 3D location of sensors 331-337. Among these are patient movement relative to table 12 (other than cardiac and respiratory motion), adjustments to the position of table 12, and adjustments to the orientations of base 7, C-arm 8, and L-arm 9. The latter two of these sources of motion are compensated for by virtue of fluoroscopic system 10 having control subsystems (not shown) commanded via control panel 15 which provide measurements of the amount of translation and rotation which has occurred, and the information is provided to method embodiment 300 to enable the coordinate system to be transformed accordingly.

However, patient motion relative to table 12 must be compensated for using other methods. One such method employs at least two external markers on the patient which are initially 3D-located during the inventive View 1/View 2 procedure described herein. After such initialization, the 2D x,y position of the external markers are monitored within the single-plane X-ray images of the patient, and the sensed x,y motion of the patient is used to transform the coordinate system accordingly. Patient motion (translational or rotational motion) which is significantly out of the x,y plane cannot be compensated for, but such patient movement is not encountered too frequently during such procedures.

While the principles of this invention have been described in connection with specific embodiments, it should be understood clearly that these descriptions are made only by way of example and are not intended to limit the scope of the invention.

The invention claimed is:

1. A method for generating a 3D map of a cardiac parameter in a region of a living heart, the method using single-plane fluoroscopic images and comprising:

placing a plurality of catheters, each having one or more radio-opaque sensors, into the region such that the locations of the sensors geometrically span the region;

capturing a first-view digitized 2D image of the region from a first fluoroscope positioned at a first angle;

identifying each of the plurality of sensors in the first-view image;

capturing a second-view digitized 2D image of the region from a second fluoroscope positioned at a second angle which is different from the first angle;

identifying each of the plurality of sensors in the second-view image;

associating each of the plurality of identified sensors in the second-view image with its corresponding identified sensor in the first-view image;

sensing and storing values of the cardiac parameter with each of the plurality of sensors;

determining the 3D location of each of the plurality of sensors from the first-view and second-view images using back-projection calculations;

associating each of the parameter values with its corresponding sensor location;

generating the parameter map from the first-view and second-view images; and displaying the parameter map on a display device.

2. The method of claim 1 wherein the first and second fluoroscopes are the same fluoroscope, and the second-view image is captured subsequent to the capture of the first-view image.

3. The method of claim 2 wherein:

capturing the first-view image includes capturing a first burst of images and selecting the first-view image from among the first burst of images; and capturing the second-view image includes capturing a second burst of images and selecting the second-view image from among the second burst of images.

4. The method of claim 3 further including determining a cardiac phase and a respiratory phase for each captured first-view and second-view image.

5. The method of claim 4 wherein selecting the first-view and second-view images includes the steps of:

identifying candidate images in the first and second bursts of images for which a cardiac-phase criterion and a respiratory-phase criterion are satisfied; and selecting a first-view image and a second-view image from the candidate images using a similarity criterion based on the cardiac phase and respiratory phase of the candidate images.

6. The method of claim 4 wherein the cardiac phase of each image is estimated using an R-wave detector to identify R-waves and measure R-wave intervals.

7. The method of claim 6 wherein selecting the first-view and second-view images includes the steps of:

identifying candidate images in the first and second bursts of images for which a cardiac-phase criterion and a respiratory-phase criterion are satisfied; and selecting a first-view image and a second-view image from the candidate images using a similarity criterion based on the cardiac phase and respiratory phase of the candidate images.

8. The method of claim 7 wherein the estimate of the cardiac phase of an image is the percentage of time, along the R-wave interval, at which an image was captured.

9. The method of claim 8 wherein the cardiac-phase criterion is satisfied if the estimated cardiac phase of an image is between 30% and 80%.

10. The method of claim 4 wherein the respiratory phase of an image is estimated from the locations acquired from a burst of images of one of the plurality of sensors to determine maximum exhalation and maximum inhalation displacement and determine a percentage of exhalation/inhalation range for the image.

11. The method of claim 10 wherein selecting the first-view and second-view images includes the steps of:

identifying candidate images in the first and second bursts of images for which a cardiac-phase criterion and a respiratory-phase criterion are satisfied; and selecting a first-view image and a second-view image from the candidate images using a similarity criterion based on the cardiac phase and respiratory phase of the candidate images.

12. The method of claim 11 wherein the respiratory-phase criterion is satisfied when the respiratory phase of an image is between 0% and 20% of maximum exhalation.

13. The method of claim 5 wherein the selecting step further includes:

for each pair of a candidate first-view image $I_i$ and a candidate second-view image $I_j$, computing the sum of the absolute value of the difference between the cardiac phases of images $I_i$ and $I_j$ and the absolute value of the difference between the respiratory phases of images $I_i$ and $I_j$, and selecting the pair of first-view and second-view images for which the sum is the minimum.

14. The method of claim 13 wherein the cardiac-phase difference and respiratory-phase difference are given relative weights prior to summing.

15. The method of claim 2 wherein the sensors are cardiac electrodes which capture electrical signals from the living heart.

16. The method of claim 15 wherein one of the plurality of electrodes is a reference electrode and the cardiac parameter mapped is local activation time (LAT).

17. The method of claim 16 wherein one or more additional LAT maps are generated using the electrode locations previously determined, the reference electrode for each such additional LAT map being selected from all electrodes in the plurality of electrodes not currently being used as a reference electrode.

18. The method of claim 17 wherein displaying the parameter map includes displaying one or more LAT maps at the same time.

19. The method of claim 16 wherein the LAT map is generated using the electrode locations previously determined and the electrical signals from the plurality of electrodes during one cardiac cycle.

20. The method of claim 19 wherein the one cardiac cycle is selected from the stored LAT values.

21. The method of claim 2 further including determining changes in the cardiac parameter values based on update criteria, and when a change occurs, generating a new parameter map using the sensor locations previously determined and updated cardiac parameter values.

22. The method of claim 21 wherein the update criteria are update thresholds and determining changes in the cardiac parameter includes:

computing for each sensor the difference between the updated parameter value and a previous parameter value; and when at least one such difference is greater than an update threshold, generating the new parameter map.

23. The method of claim 22 wherein the update threshold is the same value for each sensor.

24. The method of claim 22 wherein the update threshold for each sensor is dependent on the parameter values associated with the corresponding sensor.

25. The method of claim 24 wherein the update threshold for each sensor is twice the standard deviation of the parameter values associated with the corresponding sensor.

26. The method of claim 2 wherein the single-plane fluoroscopic images are captured by a fluoroscopic system configured to automatically determine the 3D location and orientation of a radio-opaque medical object in a living system using only single-plane fluoroscopy, such system using the determination of the 3D locations of the sensors as a portion of its initialization step.

27. The method of claim 26 wherein the radio-opaque medical object is a mapping sensor, the method further including:
adding one or more supplemental 3D locations of the mapping sensor and the corresponding parameter values associated with the supplemental 3D locations to the parameter map; and
storing the supplemental 3D locations and corresponding parameter values.

28. The method of claim 27 wherein the sensors are cardiac electrodes which capture electrical signals from the living heart, one of the plurality of electrodes is a reference electrode, and the cardiac parameter mapped is local activation time (LAT).

29. The method of claim 28 wherein one or more additional LAT maps are generated using the electrode locations previously determined, the reference electrode for each such additional LAT map being selected from all electrodes in the plurality of electrodes not currently being used as a reference electrode.

30. The method of claim 29 wherein displaying the parameter map includes displaying one or more LAT maps at the same time.

31. The method of claim 28 wherein the LAT map is generated using the electrode locations previously determined and the electrical signals from the plurality of electrodes during one cardiac cycle.

32. The method of claim 31 wherein the one cycle-length of time is selected from the stored LAT values.

33. A method for generating a 3D map of a cardiac parameter in a region of a living heart, the method using single-plane fluoroscopic images and comprising:
placing a plurality of catheters, each having one or more radio-opaque sensors, into the region such that the locations of the sensors geometrically span the region;
capturing a burst of first-view digitized 2D images of the region from a fluoroscope positioned at a first angle;
capturing a burst of second-view digitized 2D images of the region from a fluoroscope positioned at a second angle different from the first angle;
selecting a first-view image and a second-view image from the bursts such that the difference between a measure of the cardio-respiratory phase of the selected first-view image and the cardio-respiratory phase of the second-view image is minimized;
identifying each of a subset of sensors in the selected first-view and second-view images and associating each of the identified sensors in the second-view image with its corresponding identified sensor in the first-view image;
determining the 3D location of each of the identified sensors from the selected first-view and second-view images using back-projection calculations;
sensing and storing values of the cardiac parameter with each of the identified sensors;
associating each of the parameter values with its corresponding sensor location;
generating the parameter map from the selected first-view and second-view images; and
displaying the parameter map on a display device.

34. A method for generating a 3D map of a cardiac parameter in a region of a living heart into which region a plurality of catheters, each having one or more radio-opaque sensors, has been placed such that the locations of the sensors geometrically span the region, the method using single-plane fluoroscopic images and comprising:
capturing a first-view digitized 2D image of the region from a first fluoroscope positioned at a first angle;
identifying each of the plurality of sensors in the first-view image;
capturing a second-view digitized 2D image of the region from a second fluoroscope positioned at a second angle which is different from the first angle;
identifying each of the plurality of sensors in the second-view image;
associating each of the plurality of identified sensors in the second-view image with its corresponding identified sensor in the first-view image;
sensing and storing values of the cardiac parameter with each of the plurality of sensors;
determining the 3D location of each of the plurality of sensors from the first-view and second-view images using back-projection calculations;
associating each of the parameter values with its corresponding sensor location;
generating the parameter map from the first-view and second-view images; and
displaying the parameter map on a display device.

35. A method for generating a 3D map of a cardiac parameter in a region of a living heart into which region a plurality of catheters, each having one or more radio-opaque sensors, has been placed such that the locations of the sensors geometrically span the region, the method using single-plane fluoroscopic images and comprising:
capturing a burst of first-view digitized 2D images of the region from a fluoroscope positioned at a first angle;
capturing a burst of second-view digitized 2D images of the region from a fluoroscope positioned at a second angle different from the first angle;
selecting a first-view image and a second-view image from the bursts such that the difference between a measure of the cardio-respiratory phase of the selected first-view image and the cardio-respiratory phase of the second-view image is minimized;
identifying each of a subset of sensors in the selected first-view and second-view images and associating each of the identified sensors in the second-view image with its corresponding identified sensor in the first-view image;
determining the 3D location of each of the identified sensors from the selected first-view and second-view images using back-projection calculations;
sensing and storing values of the cardiac parameter with each of the identified sensors;
associating each of the parameter values with its corresponding sensor location;
generating the parameter map from the selected first-view and second-view images; and
displaying the parameter map on a display device.

* * * * *